United States Patent [19]

Walker et al.

[11] Patent Number: 5,521,163

[45] Date of Patent: May 28, 1996

[54] ANTIVIRAL PYRIMIDINE NUCLEOSIDES AND METHODS FOR USING SAME

[75] Inventors: Richard Walker; Paul Coe, both of Birmingham, United Kingdom

[73] Assignee: University of Birmingham, England

[21] Appl. No.: 227,679

[22] Filed: Apr. 14, 1994

Related U.S. Application Data

[63] Continuation of Ser. No. 104,609, Aug. 11, 1993, abandoned, which is a continuation of Ser. No. 866,204, Apr. 9, 1992, abandoned, which is a division of Ser. No. 552,191, Jul. 13, 1990, abandoned.

[51] Int. Cl.[6] .............................. A61K 31/70; C07G 3/00
[52] U.S. Cl. .............................. 514/50; 514/49; 514/931; 514/934; 536/4.1; 536/28.5
[58] Field of Search .............................. 514/49, 50, 934; 536/4.1, 28.5

[56] References Cited

U.S. PATENT DOCUMENTS

| | | | |
|---|---|---|---|
| 5,055,457 | 10/1991 | Schrinner et al. | 514/59 |
| 5,159,067 | 10/1992 | Schinazi et al. | 536/28.52 |
| 5,215,970 | 6/1993 | Datema et al. | 514/49 |
| 5,356,882 | 10/1994 | Walker et al. | 514/49 |

FOREIGN PATENT DOCUMENTS

| | | |
|---|---|---|
| 0372268 | 6/1990 | European Pat. Off. . |
| 0421777A1 | 4/1991 | European Pat. Off. . |
| 0464642A1 | 1/1992 | European Pat. Off. . |
| 0516186A2 | 12/1992 | European Pat. Off. . |
| 8808001 | 10/1988 | WIPO ........................ 514/49 |
| WO91/00867 | 1/1991 | WIPO . |
| WO92/06993 | 4/1992 | WIPO . |
| WO92/06102 | 4/1992 | WIPO . |

OTHER PUBLICATIONS

European Patent Office Offical Action mailed on Jan. 28, 1994.
Huang et al: *Nucleosides & Nucleotides*, 1993, "A Facile Synthesis of 4'-thio-2'-deoxypyrimidine Nucleosides and Preliminary Studies on Their Properties," pp. 139–147.
J. Med. Chem. 1991, 34, pp. 2361–2366, "Synthesis and Biological Activity of 2'-Deoxy-4'-thio Pyrimidine Nucleosides[1]" Secrest III et al.
J. Med. Chem. 1991, 34, pp. 2782–2786, "The Synthesis and Antiviral Activity of Some 4'-Thio-2'deoxy Nucleoside Analogues" Dyson et al.
J. Chem. Soc. Chem. Commun., 1991, pp. 741–742, "The Synthesis and Antiviral Properties of E-5-(2-Bromovinyl)-4'-thio-2'-deoxyuridine" Dyson et al.
J. Chem. Soc. Chem. Commun., 1991, pp. 1421–1422, "Stereocontrolled Preparation of Cyclic Xanthate; a Novel Synthetic Route etc." Uenishi et al.
J. Med. Chem., 1992, 35, pp. 533–538, "Synthesis and Anti–HIV Activity of 4'–Thio-2',3'–dideoxynucleosides" Secrist III et al.

*Primary Examiner*—Douglas W. Robinson
*Assistant Examiner*—James O. Wilson
*Attorney, Agent, or Firm*—Nixon & Vanderhye

[57] ABSTRACT

1'-Deoxy-5-ethyl-4'-thio-β-uridine as a compound including its physiologically functional derivatives, pharmaceutical compositions containing it and methods of treating herpes virus infections are described.

21 Claims, No Drawings

ANTIVIRAL PYRIMIDINE NUCLEOSIDES AND METHODS FOR USING SAME

This is a continuation of application Ser. No. 08/104,609, filed Aug. 11, 1993, abandoned which is a continuation of Ser. No. 07/866,204, filed Apr. 9, 1992, abandoned which is a division of Ser. No. 07/552,191, filed Jul. 13, 1990, now abandoned.

The present invention relates to pyrimidine nucleosides and their use in medical therapy particularly for the treatment or prophylaxis of virus infections.

Of the DNA viruses, those of the herpes group are the sources of the most common viral illnesses in man. The group includes herpes simplex virus (HSV), varicella zoster virus (VZV), cytomegalovirus (CMV); Epstein-Barr virus (EBV) and human herpes virus 6 (HHV6). HSV 1 and HSV 2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the newborn, in immunocompromised patients or penetration of the infection into the central nervous system can prove fatal.

Transmission of the virus is by direct physical contact between a host and a recipient; the spread of HSV infection is therefore considered a very significant social problem, particularly as no effective vaccine is yet available.

Varicella zoster (VZV) is a herpes virus which causes chickenpox and shingles. Chickenpox is the primary disease produced in a host without immunity and in young children is usually a mild illness characterised by a vesicular rash and fever. Shingles or zoster is the recurrent form of the disease which occurs in adults who were previously infected with varicella-zoster virus. The clinical manifestions of shingles are characterised by neuralgia and a vesicular skin rash that is unilateral and dermatomal in distribution. Spread of inflammation may lead to paralysis or convulsions. Coma can occur if the meninges become affected. In immunodeficient patients VZV may disseminate causing serious or even fatal illness. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host and, following a primary infection, virus may be shed for a number of years. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocomprimised for example as a result of malignancy, treatment with immunosuppressive drugs following transplantation or infection with Human Immunodeficiency virus may give rise to retinitis, pneumoitis, gastrointestinal disorders and neurological diseases. CMV infection in AIDS patients is a predominant cause of morbidity as, in 50–80% of the adult population, it is present in a latent form and can be re-activated in immuno-compromised patients.

Epstein-Barr virus (EBV) causes infectious mononucleosis, and is also suggested as the causative agent of nasopharyngeal cancer, immunoblastic lymphoma, Burkitt's lymphoma and hairy leukoplakia.

HBV is a viral pathogen of world-wide major importance. The virus is aetiologically associated with primary hepatocellular carcinoma and is thought to cause 80% of the world's liver cancer. In the United States more than ten thousand people are hospitalised for HBV illness each year, and average of 250 die with fulminant disease. The United States currently contains an estimated pool of 500,000-1-million infectious carriers. Chronic active hepatitis generally develops in over 25% of carriers, and often progresses to cirrhosis. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

We have now found that certain pyrimidine 4'-thionucleosides have potent activity against herpes viruses. The present invention therefore relates to pyrimidine 4'-thionucleosides of the following general formula

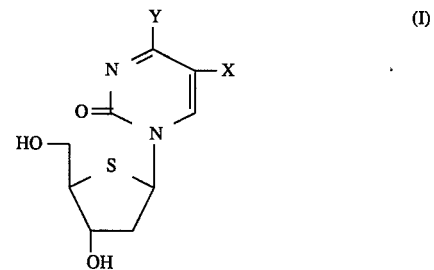

wherein Y is hydroxy or amino, and X is halo, trifluoromethyl, methyl, $C_{2-6}$ alkyl, $C_{2-6}$ alkenyl, $C_{2-6}$ haloalkenyl, including 2-bromovinyl or $C_{2-6}$ alkynyl, and physiologically functional derivatives thereof.

It will be appreciated that by virtue of the definition of the group Y the compounds of formula (I) are derivatives either of uracil or of cytosine.

It will also be appreciated that the compounds of formula (I) may exist in various tautomeric forms.

The compounds of Formula I may exist as α- or β-anomers; β-anomers are preferred.

In the definition of formula (I), references to alkyl groups include groups which, when they contain at least three carbon atoms may be branched or cyclic but which are preferably straight (particular alkyl groups include ethyl); references to alkenyl groups include groups which may be in the E- or Z- form or a mixture thereof and which, when they contain at least three carbon atoms, may be branched but are preferably straight; and references to alkynyl groups include groups which, when they contain at least four carbon atoms may be branched but which are preferably straight; particular alkenyl groups include vinyl and E-(1-propenyl) and particular alkynyl groups include ethynyl and prop-1-ynyl. References to halo-substituted groups include chloro, bromo, iodo and fluoro substituted groups and groups substituted with two or more halogens which may be the same or different, for example perhalo substituted groups (particular haloalkenyl groups include E-(2-bromovinyl)).

Preferred compounds of the formula I include those in which the group X is $C_{2-4}$ alkyl or haloalkenyl, or $C_{3-4}$ alkenyl or alkynyl. Preferred haloalkenyl groups are straight chain haloalkenyl groups having a single halogen group on the terminal carbon. Also preferred are haloalkenyl groups having a double bond in the 1-position. Of such compounds, those having a 2-halovinyl group which is in the E configuration are preferred.

Particular compounds of the invention are compounds of formula (I) and physiologically acceptable derivatives thereof wherein the pyrimidine base is selected from:

1. 5-Iodouracil
2. 5-Iodocytosine
3. 5-Ethynyluracil
4. 5-Prop-1-ynyluracil
5. 5-Vinyluracil
6. E-5-(2-Bromovinyl)uracil
7. E-5-(1-Propenyl)uracil
8. 5-Ethyluracil
9. 5-Trifluoromethyluracil
10. E-5-(2-Bromovinyl)cytosine
11. 5-Propyluracil and wherein the 4-thio sugar moiety is the 2-deoxy-4-thio-D-ribofuranose moiety.

Compounds of formula (I) having the beta configuration which are of especial interest as antiviral agents are:
E-5-(2-bromovinyl)-2'-deoxy-4'-thiouridine
2'-deoxy-5-iodo-4'-thiouridine
2'-deoxy-5-ethyl-4'-thiouridine
5-bromo-2'-deoxy-4'-thiouridine
2'-deoxy-5-propynyl-4'-thiouridine
5-chloro-2'-deoxy-4'-thiouridine
2'-deoxy-5-trifluoromethyl-4'-thiouridine
2'-deoxy-5-ethynyl-4'-thiouridine
2'-deoxy-5-E-(2-bromovinyl)-4'-thiocytidine
2'-deoxy-5-propyl-4'-thiouridine
E-2'-deoxy-5-(propen-1-yl)-4'-thiouridine Preferred compounds of formula (I) are E-5-(2-bromovinyl)-2'-deoxy-4'-thio-β-uridine and 2'-deoxy-5-ethyl-4'-thio-β-uridine. These compounds are of particular use against HSV 1 and 2, and VZV infections.

Also preferred are 2'-deoxy-5-halo-4'-thiouridine compounds, which are of particular use against CMV infections.

The above-mentioned derivatives include the pharmaceutically acceptable salts; esters and salts of esters, or any other compound which, upon administration to a human subject, is capable of providing (directly or indirectly) the antivirally active metabolite or residue thereof.

Preferred mono- and di-esters according to the invention include carboxylic acid esters in which the noncarbonyl moiety of the ester grouping is selected from straight or branched chain alkyl, (e.g. tertiarybutyl); cyclic alkyl (e.g. cyclohexyl); alkoxyalkyl (e.g. methoxymethyl), carboxyalkyl (e.g. carboxyethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); mono-, di- or triphosphate esters which may or may not be blocked, amino acids esters and nitrate esters. With regard to the above-described esters, unless otherwise specified, any alkyl moieties present in such esters advantageously contain 1 to 18 carbon atoms, particularly 1 to 4 carbon atoms, in the case of straight chain alkyl groups, or 3 to 7 carbon atoms in the case of branched or cyclic alkyl groups. Any aryl moiety present in such esters advantageously comprises a phenyl group. Any reference to any of the above compounds also includes a reference to a physiologically acceptable salt thereof.

Salts according to the invention which may be conveniently used in therapy include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. When Y represents an amino group, salts include physiologically acceptable acid addition salts, including the hydrochloride and acetate salts.

Such nucleosides and their derivatives will be hereinafter referred to as the compounds according to the invention. The term "active ingredient" as used hereafter, unless the context requires otherwise, refers to a compound according to the invention.

The present invention further includes:

a) compounds according to the invention for use in the treatment or prophylaxis of viral infections particularly herpes virus infections such as those mentioned above and more particularly HSV, VZV or CMV infections.

b) a method for the treatment or prophylaxis of a herpes virus infection such as those mentioned above in a mammal including man, particularly HSV, VZV or CMV infection which comprises treating a subject with an effective non-toxic amount of a compound according to the invention.

c) use of a compound according to the invention in the manufacture of a medicament for use in the treatment or prophylaxis of a herpes virus infection, such as those mentioned above, particularly HSV, VZV or CMV infections.

Examples of the clinical conditions which may be treated in accordance with the invention include those infections caused HSV 1 & 2, VZV, CMV or HBV described above.

We have found that compounds according to the invention have high oral bioavailability and low toxicity. This provides compounds with a favourable therapeutic index.

The compound of formula (I) wherein X is methyl and Y is hydroxy has been found to have good activity against HSV1 and 2 but to be toxic.

The compounds according to the invention may be administered to mammals including humans by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of the individual active ingredients will depend upon a number of factors including the severity of the condition to be treated and the identity of the recipient and will ultimately be at the discretion of the attendant physician. In general, however, for each of these utilities and indications, a suitable, effective dose will be in the range 0.1 to 250 mg per kilogram body weight of recipient per day, preferably in the range 1 to 100 mg per kilogram body weight per day and most preferably in the range 5 to 30 mg per kilogram body weight per day; an optimum dose is about 15 mg per kilogram body weight per day (unless otherwise indicated all weights of active ingredient are calculated as the parent compound; for salts and esters thereof the figures would be increased proportionately.) The desired dose may if desired be presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the compounds to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintergrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored an may be formulated so as to provide slow or controlled release of the active ingredient therein using, for example, hydroxpropylmethylcellulose in varying proportions to provide desired release profile.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitats or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oil can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Injection solutions and suspensions may be prepared extemporaneously from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The compounds of formula (I) may be produced by various methods known in the art of organic chemistry in general and nucleoside synthesis in particular. Starting materials are either known and readily available from commercial sources or may themselves be produced by known and conventional techniques.

The present invention further provides a process for producing a compound of formula (I) as hereinbefore defined which process comprises:

A) reacting a compound of formula (II)

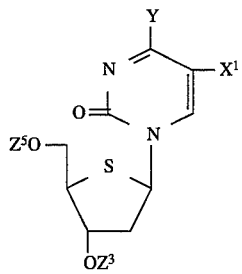

(II)

wherein $X^1$ is a precursor for the group X as defined in relation to formula (I);
Y is as defined in relation to formula (I); and
$Z^3$ and $Z^5$ are the same or different and each is hydrogen or a hydroxyl-protecting group
with a reagent or reagents serving to convert the group $X^1$ to the desired group X;

B) reacting a compound of formula (III)

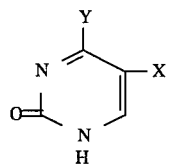

(III)

wherein X and Y are as defined in relation to formula (I) or a protected form thereof with a 4-thio sugar compound serving to introduce the 4-thio sugar moiety, or a protected form thereof, at the 1-position of the compound of formula (III); and, where necessary or desired, thereafter effecting any one or more of the following further steps in any desired or necessary order:

a) removing each of the protecting groups,
b) converting a compound of formula (I) or a protected form thereof into a further compound of formula (I) or a protected form thereof, c) converting the compound of formula (I) or a protected form thereof into a physiologically acceptable derivative of the compound of formula (I) or a protected form thereof, d) converting a physiologically acceptable derivative of the compound of formula (I) or a protected form thereof into the compound of formula (I) or a protected form, thereof, e) converting a physiologically acceptable derivative of the compound of formula (I) or a protected form thereof into another physiologically acceptable derivative of the compound of formula (I) or a protected form thereof, and f) where necessary, separating the $\alpha$ and $\beta$ anomers of the compound of formula I or a protected derivative thereof or of a physiologically acceptable derivative of a compound of formula (I) or a derivative thereof.

The term "4-thio sugar compound" is used herein to denote a compound containing the 2-deoxy-4-thio-D-ribofuranose ring wherein one or more of the hydroxyl groups thereof are optionally protected and wherein the 1-position is optionally substituted by a leaving group.

Process B may be effected, for example, by a) reaction of the compound of formula (III), or a protected form thereof, with a 4-thio sugar compound of formula (IV).

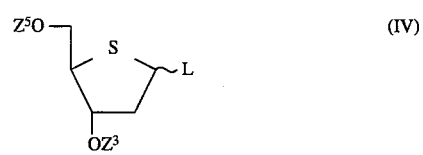

(IV)

wherein $Z^3$ and $Z^5$ are as defined above and L is a leaving group, for example halogen, e.g. chloro, acyloxy (e.g. $C_{1-6}$ alkanoyloxy such as acetoxy), or S-benzyl. In formula (IV), the groups $Z^3$ and $Z^5$ are preferably hydroxy protecting groups, particularly benzyl or toluoyl groups. The reaction may be performed using standard methods including the use of a Lewis Acid catalyst such as mercuric chloride or bromide or stannic chloride or trimethylsilyltrifluoromethanesulphonate in solvents such as acetonitrile, 1–2 dichloroethane, dichloromethane, chloroform or toluene at reduced, ambient or elevated temperature such as from $-78°$ C. to reflux; or b) reaction of the compound of formula (III), or a protected form thereof, with a compound of formula (V)

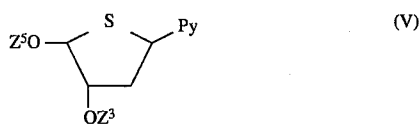

(V)

wherein $Z^3$ and $Z^5$ are as defined above and Py represents a pyrimidine base in the presence of a silylating agent such as N,O-bis-(trimethylsilyl)acetamide and in the presence of a Lewis Acid catalyst such as trimethylsilyltrifluoromethane sulphatonate in a solvent such as acetonitrile. In the compound of formula (V), Py is preferably the uracil or thymine base.

The 4-thio-sugar compound may be produced by conventional methods prior to coupling with the base or derived by modification of another sugar moiety which is already part of a nucleoside. Particular methods are as described in the Examples.

Particular methods for producing the compounds of formula (I) in accordance with the above processes will be described below and these may be combined in order to produce further compounds within formula (I).

Reference may be made to the following texts:

Synthetic Procedures in Nucleic Acid Chemistry, Eds. W. W. Zorbach R. S. Tipson, Vol. 1, Interscience, 1973; Nucleic Acid Chemistry—Improved and New Synthetic Procedures, Methods and Techniques, Eds. L. B. Townsend and R. S. Tipson, Parts 1 and 2, Wiley-Interscience, 1978 and Part 3, Wiley-Interscience, 1986; Nucleoside Analogues-Chemistry, Biology and Medical Applications Eds R. T Walker, E. De Clercq & F. Eckstein, NATO Advanced Study Institutes Series, Plenum Press, 1979;

Basic Principles in Nucleic Acid Chemistry, Eds. P.O.P Ts'O, Academic Press, 1974.

With regard to the use of protecting groups as referred to above, it will be appreciated that the particular nature of such groups will be dependent on the identity and nature of the particular group(s) to be protected and will therefore be selected in accordance with conventional techniques. Examples of protecting groups that may be generally used include acyl groups for example $C_{1-6}$ alkanoyl (e.g. acetyl) or aroyl (e.g. benzoyl or toluoyl), ether groups such as tri-$C_{1-6}$alkylsilyl (e.g. trimethylsilyl) or tert-butyl diphenylsilyl; or arylmethyl groups such as benzyl or triphenylmethyl groups.

The above groups may be removed in conventional manner, for example the acyl groups being removed advantageously under basic conditions (e.g. using sodium methoxide), the silyl ether groups being removed advantageously under aqueous or acidic conditions (e.g. using aqueous methanol to remove trimethylsilyl groups) and the arylmethyl groups being removed advantageously under reducing conditions.

Protection of hydroxy groups with trialkylsilyl, eg. trimethylsilyl, groups on the pyrimidine ring is conveniently achieved by reaction with (a) chlorotrimethylsilane together with triethylamine or with (b) hexamethyldisilazane, optionally together with chlorotrimethylsilane and/or ammonium sulphate.

The following techniques are particularly convenient:

X is halogen

5-Halopyrimidines are commercially available and may be coupled to the 4-thiosugar compound by conventional techniques, for instance by reacting a protected 5-halopyrimidine with a protected 4-thio sugar compound having a leaving group in the 1-position. The leaving group on the 4-thio sugar compound may be a halogen, benzylthio or preferably acetate group.

Reaction of the protected 4-thio sugar compound with the protected 5-halopyrimidine is conducted under conventional conditions using Lewis Acid catalysis such as by treatment with mercuric chloride or mercuric dibromide with cadmium carbonate or with stannic chloride, or preferably trimethylsilyltrifluoromethane sulphonate in toluene, acetonitrile, dichloromethane or 1,2-dichloroethane, as solvent followed by treatment as necessary with aqueous methanol (which also serves to remove the protecting groups from any hydroxyls on the pyrimidine ring).

Protecting groups may be removed by conventional techniques, for instance trimethylsilyl groups may be removed from hydroxyl groups on the pyrimidine ring by treatment with aqueous methanol, benzyl groups are removed from the hydroxyl groups on the 4-thio sugar compound by treatment with boron trichloride in dichloromethane at −78° C. and p-toluyl groups are removed from the hydroxyl groups on the sugar by treatment with sodium methoxide in methanol at room temperature.

Alternatively the 5-halo substituent may be introduced into the pre-formed 5-unsubstituted 4'-thiopyrimidine nucleosides having protected or unprotected hydroxyl groups.

When the hydroxyl groups on the 4-thio sugar compound are protected (for instance with ethers such as silyl ethers or esters such as acetate, benzoate or p-toluate esters), reaction with N-chlorosuccinimide in glacial acetic acid or with chlorine and iodobenzene and glacial acetic acid will introduce a 5-chloro substituent and reaction with iodine monochloride in dichloromethane will introduce a 5-iodo substituent, while reacting the unprotected 4'-thio sugar pyrimidine nucleoside with chlorine in carbon tetrachloride and acetic acid also introduces the 5-chloro substituent. Reaction with iodine and nitric acid also introduces the 5-iodo substituent. Reaction with bromine and acetic acid introduces a 5-bromo substituent to the unprotected nucleoside. Deprotection where necessary is by conventional techniques and is performed as the final step.

The 5-unsubstituted 4'-thionucleoside starting material of formula (II) may be produced as described above by coupling a 5-unsubstituted pyrimidine to a 4-thio sugar compound. Protection of the hydroxy groups of the 4-thio sugar moiety may be effected at any convenient stage.

X is $C_{2-6}$ alkynyl

5-Alkynyl compounds may be produced by reacting a 5-iodo nucleoside of formula (II) wherein the hydroxyl groups of the 4-thio sugar are optionally protected (for instance by reaction of the unprotected nucleoside with p-toluoylchloride in pyridine to introduce p-toluoyl ester groups on the hydroxyl groups of the 4-thio sugar) with an appropriate alkynylating agent, for example trimethylsilyl acetylene or a terminal alkyne in the presence of a palladium catalyst such as bis(triphenylphosphine) palladium dichloride, and a copper catalyst such as cuprous iodide and triethylamine and, where necessary, removal of the protecting groups using sodium methoxide in methanol [c.f.M. J. Robins et al; Can. J. Chem., 60:554 (1982)].

Alternatively the 5-alkynyl group may be introduced by reacting a 5-iodo pyrimidine with trimethylsilylacetylene or a terminal alkyne in the presence of bis(triphenylphosphine)palladium dichloride, cuprous iodide, triethylamine and dimethylformamide followed, where necessary, by removal of the protecting groups and reacting the 5-alkynyl pyrimidine of formula (III) in suitably protected form (for instance the trimethylsilyl-protected form) with a protected 4-thio sugar compound as previously described followed by deprotection of the pyrimidine and sugar moieties as required.

X is $C_{2-6}$ alkenyl

5-Alkenyl compounds may be produced by partial hydrogenation of the corresponding 5-alkynyl pyrimidine of formula (III) or of the nucleoside of formula (II) for instance using Lindlar catalyst poisoned with quinoline, and subsequently, in the case of the pyrimidine, coupling with a 4-thio sugar compound as described above.

Alternatively a 5-iodo nucleoside of formula (II) may be reacted with an appropriate alkenylating agent for example a 2-alkenoic acid ester (for instance the methyl ester) in the presence of palladium (II) acetate and triphenylphosphine to form the 5-(2-methoxycarbonyl alkenyl) derivative. The ester group is then removed by hydrolysis using sodium hydroxide forming the 2-carboxy alkenyl compound which itself is subjected to treatment with triethylamine in dimethylformamide at 100° C. to give the 5-vinyl analogue [c.f. S. G. Rahim et al., Nucleic Acids Research, 10(17):5285(1982)].

Yet another method for producing the 5-alkenyl compounds involves coupling the terminal alkene with a 5-iodo or 5-chloromercuri nucleoside of formula (II) (formed by for example reaction of the 5-unsubstituted nucleoside with mercury (II) acetate and sodium chloride), in the presence of a palladium catalyst such as palladium (II) acetate and a copper salt such as copper (I) chloride, or preferably a paladium catalyst such as dilithium palladium tetrachloride. Reaction of a 5-iodo- or 5-chloromercuri-nucleoside of formula (II) with allyl halides such as chloride or bromide in the presence of dilithium palladium tetrachloride leads to the formation of the corresponding 5-(alk-2-enyl) derivative which can be rearranged to form the 5-(alk-1-enyl) derivatives by treatment with tris(triphenylphosphine)rhodium chloride. This process may also be applied to the free pyrimidine base, which is subsequently condensed with the 4-thio sugar compound. The above processes are exemplified by J. L. Ruth & D. E. Bergstrom, J. Org. Chem, 43 (14): 2870 (1978), J. Goodchild et al., J. Med. Chem, 26: (1983), D. E. Bergstrom & J. L. Ruth, J, Am. Chem. Soc., 98: 1587 (1976) and D. E. Bergstrom & M. K. Ogawa, J. Am. Chem. Soc., 100: 8106 (1978).

X is $C_{2-6}$ haloalkenyl 5-(Haloalkenyl) substituents may be introduced into a nucleoside of formula (II) by conventional methods. For example, in order to preare 5-(2-halovinyl) compounds the corresponding 5-(2-carboxyvinyl) nucleoside is treated with an appropriate halogenating agent, for example N-halosuccinimide in aqueous potassium acetate, or with potassium carbonate in dimethylformamide when the halogen is bromo or iodo. A 5-(2-chlorovinyl) nucleoside may also be made from the corresponding 5-(2-carboxyvinyl) nucleoside using chlorine gas in, for example, dimethylformamide (DMF).

Alternatively the 5-haloalkenyl group may be introduced into the appropriate free pyrimidine base to form a compound of formula (III) which is subsequently coupled with a 4-thio compound as described above; this may be achieved for example by treating a 2,4-dimethoxy-protected 5-iodo-pyrimidine with an 2-alkenoic acid ester in the presence of palladium (II) acetate, triphenylphosphine and dioxane followed by removal of the methoxy protecting groups, hydrolysis of the ester with sodium hydroxide and reaction of the resulting 5-(2-carboxyvinyl) derivative with N-halo-succinimide (where halo is bromo or iodo) or chlorine gas (where halo is chloro) in the presence of a base such as sodium hydrogen carbonate in dimethylformamide. The 5-(2-carboxyvinyl) compound may also be produced by treating an unprotected 5-(hydroxymethyl)pyrimidine of formula (III) with an oxidising agent such as persulphate or manganese dioxide to form the corresponding aldehyde and followed by treatment of the aldehyde with malonic acid. The above processes are exemplifed by A. S. Jones et al, Tetrahedron Letts, 45; 4415 (1979) and P. J. Bart et al, J. Chem. Soc. Perkin Trans 1, 1981, 1665.

The 5-(2-haloalkenyl) base may alternatively be made by a novel route starting with a 2,4-dimethoxy protected 5-bromopyrimidine. This may be converted to the corresponding 5-lithium derivative by treatment with an organolithium reagent, preferably n-butyllithium at reduced temperature such as −70° C. in an ethereal solvent such as diethylether. Reaction of the lithio derivative in situ with an appropriate ester of formic acid, such as ethyl formate at reduced temperature such as −70° C. gives rise to the corresponding 5-formyl compound. Treatment of the formyl compound with malonic acid as described above give rise to the 5-(2-carboxyvinyl) derivative. Similar halogenation gives rise to the required 5-(2-haloalkenyl) compound which is in the 2,4-dimethoxy protected from. Deprotection can then be carried out by conventional techniques.

5-Halovinyl compounds having more than one halogen substituent may be produced from a 5-halo-substitued 2,4-dimethoxy protected pyrimidine of formula (III) by reaction with a strong base such as butyl lithium and the resulting lithio derivative treated with the appropriate haloalkene followed by removal of the protecting groups and coupling to the 4-thio sugar compound as described above [c.f. P. L. Coe et al., J. Med. Chem. 25:1329 (1982)].

Alternatively, the halogen atoms may be introduced sequentially into a 5-substituent of the pyrimidine base. Thus, for example treatment of 5-acetyl uracil with a chlorinating agent such as phosphorus oxychloride provides the 5-(1-chlorovinyl) group with simultaneous chlorination of the hydroxyl groups of the pyrimidine base. Treatment with potassium ethoxide then hydrogen chloride and finally bromine leads to bromination of the 5-unsaturated side chain of the pyrimidine base with simultaneous conversion of the 2,4-dichloro groups on the pyrimidine ring to form the corresponding uracil derivative. The resulting pyrimidine base can then be coupled to the 4-thio sugar compound as described above [c.f. P. J. Barr et al. Nucleic Acids Res. 3: 2845 (1976) and P. J. Barr et al., J. Chem. Soc. Perkin Trans 1, 1981: 1665].

X is $C_{2-6}$ alkyl

5-$C_{2-6}$ Alkyl eg. 5-ethyl substituted nucleosides may be produced by hydrogenation of the corresponding 5-alkynyl or 5-alkenyl pyrimidine base followed by coupling to the 4-thio sugar compound. Conventional hydrogenation conditions, such as hydrogen over palladium/charcoal catalysts, may be adopted.

X is trifluoromethyl

5-Trifluoromethyl uracil is commercially available and this may be condensed with a 4-thio sugar compound in accordance with process B described above. The 5-trifluoromethyl cytosine analogue may be made from the uracil compound/using an analogous procedure to that described by Sung as mentioned below.

The above reactions are all suitable for producing uracil nucleosides; most of such reactions may also be used to form cytosine nucleosides. When this is not convenient or possible, cytosine analogues can be prepared most conveniently from the uracil compounds using an analogous procedure to that described by W. L. Sung, J. Chem. Soc. Chem. Commum., 1981, 1089]: for example the acetylated uracil nucleoside (produced for instance by reactions as described above and acetylated using acetic anhydride in pyridine) is treated with p-chlorophenylphosphorodichloridate, 1,2,4-triazole and pyridine to produce the 4-(1,2,4-triazol-1-yl) derivative which is then treated with ammonia in dioxane (which also removes the 4-thio sugar protecting group(s)) to form the corresponding unprotected cytosine 4'-thionucleoside.

The derivatives of the compounds of formula (I) may be prepared in conventional manner. For example, esters may be prepared by treating a compound of formula (I) with an appropriate esterifying agent, for example, an acyl halide or anhydride. Salts may be prepared by treating a compound of formula (I) with an appropriate base, for example an alkali metal, alkaline earth metal or ammonium hydroxide, or where necessary, an appropirate acid, such as hydrochloric acid or an acetate, eg. sodium acetate.

The anomers of compounds of the formula I may be separated by conventional means, for example by chromatography or fractional crystallisation.

In a further aspect of the invention, compounds of the formula (IV) may be made by ring closure of a compound of the formula (VI)

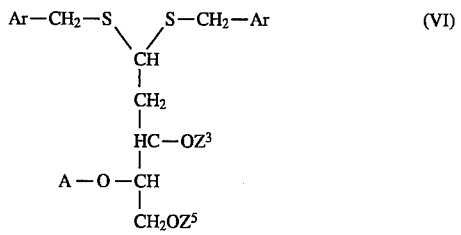

where $Z^3$ and $Z^5$ are hydroxyl protecting groups such as benzyl optionally substituted on the phenyl ring by one or more halogen atoms, $C_{1-4}$ alkyl eg. methyl, $C_{1-4}$ haloalkyl, $C_{1-4}$ alkoxy, nitro or amino groups. The group A is a leaving group, for example an organosulphonyl group such as an optionally substituted alkyl- or aryl- sulphonyl group, for instance methanesulphonyl, a haloalkylsulphonyl group (eg. trifluoromethyl-sulphonyl) and optionally substituted phenylsulphonyl (eg. toluylsulphonyl or bromobenzenesulphonyl), and Ar is an optionally substituted aryl group, for example optionally substituted phenyl or toluyl. Optional substituents of the aryl groups include one or more halogen atoms, $C_{1-4}$ alkyl eg. methyl, $C_{1-4}$ haloalkyl, $C_{1-4}$ alkoxy, nitro or amino groups. The ring closure may be performed under appropriate basic conditions. Suitable conditions include those described by J. Harness and N. A. Hughes (Chem. Comm. 1971, 811), which includes the use of sodium iodide and barium carbonate.

The compound of the formula (VI) may be made from a compound of formula (VII)

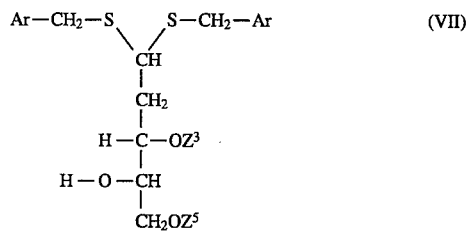

where Ar, $Z^3$ and $Z^5$ are as defined above. Conversion of a compound of formula (VII) to a compound of formula (VI) is carried out according to standard procedures such as treatment with an appropriate optionally substituted alkyl- or aryl- sulphonyl halide, eg. methanesulphonylchloride in a basic solvent such as pyridine.

The compound of formula (VII) may be made from a compound of formula (VIII):

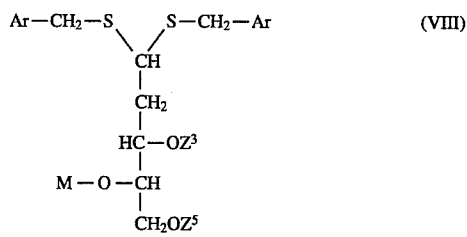

where Ar, $Z^3$ and $Z^5$ are as defined above and M is a hydroxyl protecting group which may be removed under conditions which leave the —S—CH$_2$—Ar groups and the groups $Z^3$ and $Z^5$ in place.

Preferably, the group M is a group of the formula Ar$^1$—CO— where Ar$^1$ is a phenyl group which may be optionally substituted by any of the substituents described above for the group Ar. Removal of the group M may be performed under standard conditions, for example with a base such as an alkali metal alkoxide, for instance sodium methoxide in methanol.

The compounds of formula (VIII) may be obtained by the concomitant inversion and derivatization of the 4-hydroxy group of a compound of formula (IX)

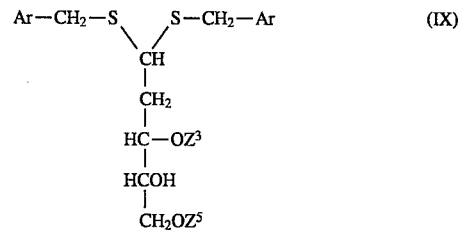

wherein Ar, $Z^3$ and $Z^5$ are as defined above. The inversion and derivatization may be effected by reacting the compound of formula (IX) with a derivative of the group M, such as an acid of the formula Ar$^1$—COOH, for example benzoic acid (or a reactive derivative thereof) where Ar$^1$ is as defined above. The reaction is performed typically at room temperature and under neutral conditions in a suitable polar solvent, for instance tetrahydrofuran. Preferably the Mitsunobu reaction is used for the inversion and derivatization; diethyl azodicarboxylate (DEAD) and triphenylphosphine are used as coreactants together with the acid Ar$^1$—COOH.

The compound of formula (IX) may be made from a glycoside compound of formula (X)

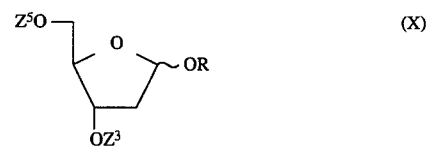

where $Z^3$ and $Z^5$ are as defined above and R is a $C_{1-4}$ hydrocarbyl group, eg. a $C_{1-4}$ alkyl group, preferably methyl. The compound of the formula IX is reacted under acid conditions at an elevated temperature with a compound of formula Ar—CH$_2$—SH, where Ar is as defined above. Suitably, hydrochloric acid is used as the acid which may be in aqueous or anhydrous form. Preferably the elevated temperature is from 30° C. to 60° C., for example 40° C. When Ar is a phenyl group, the compound Ar—CH$_2$—SH will be benzyl thiol.

Compounds of the formula (X) may be made from a compound of formula (XI)

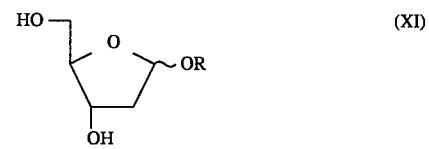

where R is a defined above. The hydroxyl groups of the compound of formula (XI) are protected under conventional conditions with the reactive derivative of the groups $Z^3$ and $Z^5$. Suitably, the bromo derivative may be used. Thus when $Z^3$ and $Z^5$ are benzyl groups, benzyl bromide may be used. The reaction may be performed in an organic solvent such as tetrahydrofuran in the presence of a suitable base such as sodium hydride and a phase transfer catalyst such as tetrabutylammonium iodide.

Compounds of the formula (XI) may be made by standard techniques from 2-Deoxy-D-ribose, which is commercially available. 2-Deoxy-D-ribose may be reacted with an alcohol of formula R—OH (where R is as defined above) in the presence of an acid. Hydrochloric acid is suitable. When R is a methyl group, the alcohol R—OH will be methanol.

The conversion of 2-deoxy-D-ribose to a compound of formula (XI) will also produce a small proportion of the corresponding pyranoside compound, substituted at the 1-position by the group —OR. This may remain in the reaction mixture during the converions of (XI) to (X), (X) to (IX) and the subsequent reactions described above and it will undergo analogous reactions. These by-products may be separated at any convenient step by conventional means, eg. chromatography.

The compound of the formula VII may also be made directly from the compound of formula IX using a Mitsunobu reaction under conditions analogous to those described by D. R. Williams et al, JACS (1990) 112, 4552.

The invention is illustrated by the following non-limiting Examples

EXAMPLE A

Preparation of Methyl 3,5-di-O-benzyl-2-deoxy-D-erythropentoside

To a solution of 2-deoxy-D-ribose (50 g, 373 mmol) in dry methanol (900 ml) was added a 1% solution of dry hydrogen chloride in methanol (100 ml). The mixture was kept in a stoppered flask for 30 minutes after which the reaction was stopped by adding, with vigorous stirring, silver carbonate (10 g). The mixture was filtered by gravity and the colourless filtrate evaporated to a syrup using a dry rotary evaporator. Residual methanol was then removed by repeated evaporation with dry THF. The syrup was then dissolved in dry THF (470 ml). Under an atmosphere of dry nitrogen, at 0° C., with stirring sodium hydride in a 50% oil-dispersion (39.4 g, 821 mmol) was slowly added to the THF mixture. Next, dry tetrabutylammonium iodide (30.3 g, 82.1 mmol) was added followed by benzyl bromide (140 g, 821 mmol), which was added over 1 hour. After stirring for 60 hours at room temperature, with exclusion of moisture, TLC (hexane-ethyl acetate [4:1]) showed almost complete conversion to two faster moving components ($R_f$ 0.47 and 0.36). The THF was removed in vacuo, the residue dissolved in dichloromethane and then poured into ice/water. The dichloromethane solution was extracted from this mixture and then dried over magnesium sulphate. The dichloromethane was evaporated under reduced pressure and the resulting residue applied to a silica gel column eluted with hexane-ethyl acetate (4:1). Combination of the appropriate fractions gave the α (Rf 0.36) and β ($R_f$ 0.47) isomers of the title product as a clear, colourless syrup
NMR SPECTRA
α - isomer
($^1$H) δ ($d_6$DMSO):7.56-7.17 (10H,d,aromatic), 5.12- 5.00 (1H,q;H-1), 4.60-4.45 (4H,m, PhCH$_2$O), 4.40-3.86 (2H,m, H-3, H-4), 3.58-3.42 (2H,d,H-5), 3.40 (3H,s,CH$_3$),2.40-1.80 (2H,m,H-2).
($^{13}$C) δ (CDCl$_3$): 128.3-127.6 (aromatic), 105.2 (C- 1), 82.1 (C-3 or C-4), 78.6 (C-3 or C-4), 73.4 (PhCH$_2$O), 71.5 (PhCH$_2$O), 70.2 (C-5), 55.1 (OMe), 38.9 (C-2).
β - isomer
($^1$H) δ ($d_6$DMSO):7.50- 7.20 (10H,d,aromatic), 5.18-5.02 (1H,q,H-1), 4.65-4.43, (4H,d, PhCH$_2$O), 4.43-4.00 (2H,m, H-3,H-4), 3.60-3.42 (2H,m,H-5), 3.30 (3H,s,CH$_3$), 2.45-2.05 (2H,m,H-2) .
($^{13}$C) δ (CDCl$_3$):128.3-127.6 (aromatic), 105.4 (C-1), 82.8 (C-3 or C-4), 80.0 (C-3 or C-4), 73.3 (PhCH$_2$O), 72.0 (PhCH$_2$O), 70.2 (C-5), 54.9 (OMe), 39.3 (C-2).

Preparation of 3,5-di-O-benzyl-2-deoxy-D-erythro-pentose dibenzyl dithioacetal Concentrated hydrochloric acid (150 ml) was added dropwise to a stirred mixture of methyl 3,5-di-O-benzyl-2-deoxy D-erythro-pentoside (77.5 g, 236 mmol) and benzyl thiol (147 g, 1.19 mol) at room temperature. The temperature was then raised to 40° C. and the mixture stirred for 18 hours. At the end of this time TLC (hexane-ethyl acetate [4:1]) showed two faster moving minor components ($R_f$ 0.58 and 0.53), a major component ($R_f$0.29) and a slower moving minor component ($R_f$0.22). The mixture was dissolved in chloroform, poured into ice/water, neutralised with sodium hydrogen carbonate and extracted with chloroform. The chloroform extracts were dried over magnesium sulphate and the chloroform was evaporated under reduced pressure. The residue was applied to a silica gel column which was eluted with hexane-ethyl acetate (4:1). The first component to be eluted from the column, as a clear colourless syrup was the α, β anomers of benzyl 3,5-di-O-benzyl-2-deoxy-1-thio-D-erythro-pentofuranoside.
NMR SPECTRUM
($^1$H) δ ($d_6$DMSO):7.43-7.15 (15H,m,aromatic), 5.12-4.94 (1H,m,H-1), 4.59-4.36 (4H,m,PhCH$_2$O), 4.12-3.30 (6H,m, H- 3,H-4,H-5,PhCH$_2$S), 2.35-1.35 (2H,m,H-2).
ELEMENTAL ANALYSIS
Found: C,74.4; H,6.5. $C_{26}H_{28}O_3S$ requires C,74.3; H,6.7%
MASS SPECTRUM
m/z 420 M$^+$, 297 [M-SBn]$^+$, 3-noba matrix.
The title product was the second component to be eluted from the column as a clear syrup (109 g,85%).
NMR SPECTRUM
($^1$H) δ ($d_6$DMSO):7.35-7.05 (20H,m,aromatic), 4.97-4.95 (1H,d,OH-4), 4.47-3.95 (4H,m,PhCH$_2$O) ,3.81-3.66 (7H,m, H-1,H-3,H-4, PhCH$_2$S), 3.44-3.32 (2H,d,H-5), 2.10-1.83 (2H,m,H-2).
ELEMENTAL ANALYSIS
Found: C,73.0; H,6.5. $C_{33}H_{36}O_3S_2$ requires C,72.8; H,6.7%.
MASS SPECTRUM
m/z 298 [M-2.SBn]$^+$, 3-noba matrix
SPECIFIC ROTATION
$[\alpha]_D^{25}=-101.8°$ (c1.2 in EtOH)

Preparation of 4-O-benzoyl-3,5-di-O-benzyle-2-deoxy-L-threopentose dibenzyl dithioacetal To a solution of 3,5-di-O-benzyl-2-deoxy-D-erythropentose dibenzyl dithioacetal (54.1 g,99.3 mmol),triphenylphosphine (39.1 g, 149 mmol) and benzoic acid (18.2 g, 149 mmol) in dry THF (800 ml) was added a solution of DEAD (26.0 g, 149 mmol) in dry THF (200 ml) dropwise, with stirring, at room temperature.

After stirring at room temperature for 18 hours, TLC (hexane-ethyl acetate [4:1]) revealed a faster moving component (Rf 0.56) and slower moving starting material (Rf 0.36). The THF was removed in vacuo and the residue applied to a silica gel column eluted with hexane-ethyl acetate (85:15). Combination of the appropriate fractions gave the title product as a white solid. Starting material could also be recovered.
NMR SPECTRUM
($^1$H) δ ($d_6$DMSO):7.99-6.98 (25H,m,aromatic), 5.39-5.22 (1H,m,H-4), 4.54-4.04 (4H,m,PhCH$_2$O), 4.01-3.62 (8H,m,H-1,H-3,H-5,PhCH$_2$5), 2.17-1.84 (2H,m,H-2).

ELEMENTAL ANALYSIS

Found: C,74.3; H,6.4. $C_{40}H_{40}O_4S_2$ requires C,74.0; H, 6.2% MASS SPECTRUM m/z 525 [M-SBn]$^+$, 435 [M-2 SBn]$^+$, glycerol matrix.

SPECIFIC ROTATION $[\alpha]_D^{25}$=51.6° (c0.7 in $CH_2Cl_2$).

Preparation of
3,5-di-O-benzyl-2-deoxy-L-threopentose dibenzyl dithioacetal

To a solution of 4-O-benzoyl-3,5-di-O-benzyl-2-deoxy-L-threopentose dibenzyl dithioacetal (88.8 g, 137 mmol) in dichloromethane (500 ml) was added a solution of sodium methoxide (11.1 g, 206 mmol) in methanol (205 ml) dropwise, with stirring, at 0° C. The reaction mixture was then allowed to warm to room temperature over a period of 3 hours. At the end of this time TLC (hexane-ethyl acetate [4:1]) revealed complete conversion to a slower moving component (Rf 0.31). The mixture was then poured into a 5% solution of $NaH_2PO_4$ and extracted with dichloromethane. The dichloromethane extracts were then washed with a 5% solution of sodium hydrogen carbonate and water, dried (magnesium sulphate) and evaporated. The crude title product was applied to a silica gel column eluted with hexane-ethyl acetate (4:1). Combination of the appropriate fractions gave the title product as a clear colourless syrup.

NMR SPECTRUM ($^1$H) δ ($d_6$DMSO):7.34-7.06 (20H,m,aromatic), 4.88-4.86 (1H,d,OH-4), 4.55-4.00 (4H,m,PhCH$_2$O), 4.83-3.32 (9H,m, H-1,H-3,H-4,H-5, PhCH$_2$S), 2.08-1.84 (2H,m,H-2).

ELEMENTAL ANALYSIS

Found: C,72.6; H,6.9. $C_{33}H_{36}O_3S_2$ requires C,72.8; H,6.7%

MASS SPECTRUM m/z 297 [M-2.SBn+H]$^+$, glycerol matrix.

SPECIFIC ROTATION $[\alpha]_D^{25}$=−75.6° (c1.9 in EtOH).

Preparation of
3,5-di-O-benzyl-2-deoxy-4-O-methane-sulphonyl-L-threo-pentose dibenzyl dithioacetal To a solution of 3,5-di-O-benzyl-2-deoxy-L-threo-pentose dibenzyl dithioacetal (61.4 g, 113 mmol) in dry pyridine (700 ml) was added methanesulphonyl chloride (19.4 g, 169 mmol) in dry pyridine (200 ml) dropwise, with stirring, at 0° C. The temperature of the mixture was raised to room temperature and stirring continued for 18 hours. The pyridine was then removed in vacuo and the residue dissolved in dichloromethane. The dichloromethane extracts were then successively washed with 2M hydrochloric acid, 1M sodium carbonate and water, dried (magnesium sulphate) and evaporated to give the title product as a thick viscous syrup. A sample of this was crystallised from hexane-ethyl acetate to give the title product as white crystals, m.p 82°–83° C.

NMR SPECTRUM ($^1$H) δ ($d_6$DMSO): 7.64-6.89 (20H,m,aromatic), 4.88-4.64 (1H,m,H-4), 4.60-4.09 (4H,m,PhCH$_2$O), 4.05-3.43 (5H,m,H-1,H-3,H-5,PhCH$_2$S), 3.11 (3H,s,CH3), 2.12-1.80 (2H,m,H-2)

ELEMENTAL ANALYSIS

Found: C,65.5; H,6.1 $C_{34}H_{38}O_5S_3$ requires C,65.6; H,6.2%

MASS SPECTRUM m/z 499 [M-SBn]$^+$, 393 [M-SBn-OBn+H]$^+$, glycerol matrix.

SPECIFIC ROTATION $[\alpha]_D^{25}$=−58.4° (c2.4 in $CH_2Cl_2$).

Preparation of benzyl
3,5-di-O-benzyl-2-deoxy-1,4-dithio-D-erythro-pentofuranoside A suspension of 3,5-di-O-benzyl-2-deoxy-4-O-methanesulphonyl L-threo-pentose dibenzyl dithioacetal (29.4 g, 47.4 mmol), sodium iodide (74.0 g, 494 mmol), barium carbonate (148 g, 750 mmol) and dry acetone (1L) was boiled under reflux for 42 hours. At the end of this time the suspension was filtered and the solids were washed with chloroform. The filtrate was sequentially washed with water, sodium thiosulphate solution (5%) and water, dried (magnesium sulphate) and evaporated. The resultant residue was applied to a silica gel column, eluted with hexane-ethyl acetate (9:1). Combination of the appropriate fractions gave the title product as a clear, slightly yellow, syrup, and recovered starting material.

NMR SPECTRA ($^1$H) δ ($d_6$DMSO):7.50-7.12 (15H,m,aromatic), 4.66-4.13 (6H,m,H-1,H-4,PhCH$_2$O), 4.09-3.35 (5H,m,H-3, H-5,PhCH$_2$S), 2.44-1.94 (2H,m,H-2).

Major anomer ($^{13}$C) δ (CDCl$_3$):129.0-127.1 (aromatic), 83.04 (C-1), 73.1 (PhCH$_2$O), 73.1 (PhCH$_2$O), 71.0 (C-3), 53.2 (PhCH$_2$S), 49.9 (C-4), 41.3 (C-5), 37.0 (C-2).

Minor anomer ($^{13}$C) δ (CDCl$_3$):129.0-127.1 (aromatic), 82.7 (C-1), 72.9 (PhCH$_2$O), 72.9 (PhCH$_2$O), 71.6 (C-3), 53.0 (PhCH$_2$S), 49.0 (C-4), 41.0 (C-5), 37.0 (C-2).

ELEMENTAL ANALYSIS

Found: C,71.8;H,6.7;S,14.4. $C_{26}H_{28}O_2S_2$ requires C,71.5;H,6.5;S,14.7%

MASS SPECTRUM m/z 437 [M+H]$^+$, 345 [M-Bn]$^+$, 329 [M-OBn]$^+$, 313 [M-SBn]$^+$, 223 [M-SBn-Bn+H]$^+$, glycerol matrix.

Preparation of 3',5'-di-O-benzyl-4'-thio-thymidine and its α-anomer

A suspension of benzyl 3,5-di-O-benzyl-2-deoxy-1,4-dithio-D-erythro-pentofuranoside (22.5 g, 51.6 mmol), his TMS-thymine (46 g, 170 mmol), mercuric bromide (20.5 g, 56.7 mmol), cadmium carbonate (29.3 g, 170 mmol) and dry toluene (1L) was boiled under reflux, with stiring, for 24 hours. The hot mixture was then filtered and the solids were washed with toluene. The filtrate was successively washed with potassium iodide solution (30%) and water and then evaporated. The residue was taken up in 4:1 methanol-water, stirred for 30 minutes, the suspension filtered and the filtrate evaporated. The residue was applied to a silica gel column (hexane-ethyl acetate (1:1)) and combination of the appropriate fractions gave the title product as a clear colourless syrup. $^1$H NMR indicated the ratio of α- to β- anomers to be 2.8:1. Further column chromatography gave more of the separated anomers. The first compound to be eluted from the column was 3',5'-di-O-benzyl-4'-thio-thymidine as a colourless syrup. This could be crystallised from methanol to give colourless crystals m.p. 140°–142° C.

NMR SPECTRUM ($^1$H) δ ($d_6$DMSO):11.36 (1H,s,NH), 7.69 (1H,s,H-6), 7.48-7.22 (10H,m,aromatic), 6.33-6.27 (1H,t,H-1') 4.61-4.51 (4H,m,PhCH$_2$O), 4.30 (1H,s,H-3'), 3.76-3.66 (3H, m,H-4',H-5') 2.42-2.32 (2H,m,H-2), 1.66 (3H,s,CH$_3$).

UV SPECTRUM max 269.1 nm (ε,14,300).

ELEMENTAL ANALYSIS

Found: C,66.0;H,66.0;N,6.3. $C_{24}H_{26}N_2O_4S$ requires C,65.7;H,6.0;N,6.4%

MASS SPECTRUM m/z 439 [M+H]+, 347 [M-Bn ]+, 331 [M-OBn]+, 3-noba matrix.

The next component to be eluted from the column was the α-anomer, as a colourless syrup.

NMR SPECTRUM ($^1$H) δ (d6DMSO): 11.28 (1H,s,NH), 7.95 (1H,s,H-6), 7.43-7.20 (10H,m, aromatic), 6.25-6.21 (1H,d,H-1'), 4.66-4.47 (7H,m, Ph CH$_2$O), 4.25 (1H,s,H-3'), 4.10-4.06 (1H,m, H-4'), 3.57-3.42 (2H,m,H-5'), 2.68-2.26 (2H,m,H-2'), 1.55 (3H, s, CH$_3$).

UV SPECTRUM

Max 268.1 nm (ε, 10,900).

ELEMENTAL ANALYSIS

Found: C,65.4; H,6.1;N,6.7;S,7.4. $C_{24}H_{26}N_2O_4S$ requires C,65.7; H, 6.0; N 6.4; S,7.3%.

MASS SPECTRUM m/z 439 [M+H]+, 461 [M+Na]+, 3-noba matrix.

Preparation of β-4'-thio-thymidine

To a 2M boron trichloride solution in dry dichloromethane (55 ml) cooled to −78° C., was added a solution of β-3',5'-di-O-benzyl-4'-thio-thymidine (1.6 g, 3.7 mmol) in dry dichloromethane (30 ml). Stirring was continued for 5 hours at −78° C. This was then followed by the dropwise addition of a 1:1 methanol-dichloromethane solution (200 ml) over 40 minutes. The reaction mixture was allowed to warm to room temperature over 1 hour and the solvent removed in vacuo and coevaporated with dry methanol (3×30 ml). The residue was applied to a silica gel column eluted with chloroform-methanol (85:15) to give the title title product. This could be crystallised from methanol to give colourless crystals m.p. 208°-209° C.

NMR SPECTRUM ($^1$H) δ (d$_6$DMSO) 11.34 (1H,s,NH), 7.81 (1H,s,H-6), 6.32-6.26 (1H,t,H-1'), 5.26-5.25 (1H,d,OH-3'), 5.20-5.16 (1H,t, OH-S'), 4.40-4.35 (1H,m,H-3') 3.18-3.16 (3H,m,H-4', H-5 2.25- 2.13 (2H,m,H-2'), 1.80 (3H,s,CH$_3$).

UV SPECTRUM max 270.5 nm (ε,10,300).

ELEMENTAL ANALYSIS

Found: C,46.2; H,5.3;N,10.6 $C_{10}H_{14}N_2O_4S$ requires C,46.5; H,5.5; N,10.9%.

MASS SPECTRUM m/z 259 [M+H]+, 3-noba matrix.

Preparation of benzyl 2-deoxy-1,4-dithio-3,5-di-O-p-toluoyl-D-erythro-pentofuranoside To a 2M boron trichloride solution in dry dichloromethane (150 ml) cooled to −78° C., was added a solution of benzyl 3,5-di-O-benzyl-2-deoxy-1,4-dithio-D-erythro-pentofuranoside (4.2 g, 10 mmol) in dry dichlormethane (100 ml), dropwise, over 30 minutes. Stirring was continued for 5 hours at −78° C. This was then followed by the dropwise addition of a 1:1 methanol-dichloromethane solution (200 ml) over 40 minutes. The reaction mixture was allowed to warm to room temperature over 1 hour and the solvent removed in vacuo and coevaporated with dry methanol (3×30 ml). The crude residue was dissolved in dry pyridine (25 ml), cooled to 0° C., and a solution of p-toluoyl chloride (4.6 g, 30 mmol) in dry pyridine (25 ml) added, dropwise, with stirring. The pyridine was removed in vacuo, the residue extracted with chloroform, and the extract successively washed with 2M hydrochloric acid, 1M sodium carbonate and water, dried (magnesium sulphate) and evaporated. The residue was applied to a silica gel column eluted with hexane-ethyl acetate (9:1) to give the title product as a clear, slightly yellow, syrup (2.5 g, 53%).

NMR SPECTRUM ($_1$H) δ (d6DMSO): 7.94-7.25 (13H,m,aromatic), 5.68-5.62 (1H,m,H-1') 4.74-4.66 (1H,m,H-3'), 4.39-3.83 (6H,m, H-3 ',H-4',H-5', PhCH$_2$S), 2.51-2.25(2H,m,H-2'), 2.39 (6H, s,CH$_3$).

ELEMENTAL ANALYSIS

Found: C,67.2;H,5.7. $C_{28}H_{28}O_4S_2 \cdot \frac{1}{2}H_2O$ requires C,67.0;H,5.8%.

MASS SPECTRUM m/z 515 [M+Na]+, 401 [M-Bn]+, 369[M-SBn]+ ·357 [M-OpTol]+, 3-noba matrix.

Preparation of E-5(2-bromovinyl-2'-deoxy-4'-thio-3',5'-di-O-p-toluoyl-uridine and its α-anomer To a solution of benzyl 2-deoxy-1,4-dithio-3,5-di-O-p-toluoyl-D-erythro-pentofuranoside (1.4 g,2.8 mmol) in carbon tetrachloride (15 ml) was added a solution of bromine (0.49 g, 3.1 mmol) in carbon tetrachloride (15 ml) with stirring at room temperature. After 5 minutes the mixture was concentrated under diminished pressure and then carbon tetrachloride (5 ml) was added and the mixture was evaporated to remove the excess bromine. The evaporation procedure was repeated four times. The resulting syrupy bromide was unstable and was used directly in the next step.

To a solution of the bromide in carbon tetrachloride (10 ml) was added the his TMS-derivative of E-5-(2-bromovinyl)uracil (1.7 g, 4.7 mmol) in carbon tetrachloride (10 ml). The mixture was stirred until homogenous, evaporated and the residue heated for I hour at 90°-100° C. The cooled, dark residue was dissolved in 4:1 methanol-water (30 ml), the solution boiled for 15 minutes under reflux and then evaporated. The residue was triturated with chloroform (40 ml) and the solid 5-(2-bromovinyl) uracil that separated filtered off. The filtrate was successively washed with aqueous sodium hydrogen carbonate and water, dried (sodium sulphate) and evaporated. The residue was applied to a silica gel column eluted with hexane-ethyl acetate (3:2). Combination of the apporpirate fractions gave the title product as a white solid. 1H NMR indicated the ratio of α - to β -anomers to be 1.8:1. Further column chromatography (chloroform-propan-2-ol (98:1)) gave more separated anomers. The first compound to be eluted from the column was E-5-(2-bromovinyl)-2'-deoxy-4'-thio-3'5'di-O-p-toluoyl-uridine which could be crystallised from methanol to give colourless crystals m.p. 182°-184°-C.

NMR SPECTRUM ($^1$H) δ(d$_6$DMSO): 11.73 (1H,s,NH) ,8.10 (1H,s,H-6) , 7.94-7.86 (4H,m, aromatic), 7.39-7.19 (SH,m, aromatic and vinylic H), 6.89 (1H,d,vinylic H,J=5 Hz), 6.45-6.40 (1H,t, H-1'), 5.85-5.80 (1H,m,H-3'), 4.71-4.53 (2H,m, H-5'), 4.00-3.92 (1H,m, H-4'), 2.83-2.50 (2H,m, H-2'), 2.39 (6H,s, CH$_3$).

UV SPECTRUM max 241.6 nm (ε,34,960), 296.9 nm (E,10,100 min 271.4 nm (ε,7,700).

MASS SPECTRUM m/z 586 [M+H]+, thioglycerol matrix. The next component to be eluted from the column was the α -anomer which could be crystallised from methanol to give colourless crystals m.p.176°-172° C.

NMR SPECTRUM ($^1$H) δ(d$_6$DMSO) 11.64 (1H,s,NH),8.36 (1H,s,H-6), 7.91-7.77 (4H,m,aromatic), 7.36-7.22 (5H,m,aromatic, vinylic H) 6.80 (1H,d,vinylic H, J=5 Hz), 6.29-6.27 (1H,d,H1') 5.74-5.62 (1H,m,H-3')4.48-4.39 (3H,m,H-4',H-5'), 2.94-2.85 (2H,m,H-2'), 2.37 (6H,s,CH$_3$).

UV SPECTRUM
max 241.6 nm (ε,47,000) 296.1 nm (ε,12,500).
min 273.1 nm (ε,10,000)

ELEMENTAL ANALYSIS
Found C, 54.4; H,4.4;N,4.5. C$_{27}$H$_{25}$BrN$_2$O$_6$S½H$_2$O requires
C,54.6;H,4.2;N,4.7%.

MASS SPECTRUM
m/z 586 [M+H]$^+$, thioglycerol matrix.

EXAMPLE 1

Preparation of E-5-(2-bromovinyl-2'-deoxy-4'-thiouridine and its α-anomer

E-5-(2-bromovinyl)-2'-deoxy-4'-thio-3',5'-di-O-p-toluoyl-uridine (200 mg, 0.34 mmol) was dissolved in a solution of sodium methoxide in methanol (7.5 ml,0.1 m) and the mixture allowed to stand at 22° C. for 24 hours. The solution was neutralised by careful addition of Dowex 50 ion exchange resin (H$^+$form) to pH6. The resin was filtered off and washed with methanol and the filtrate and washings evaporated to a white solid. This was applied to a silica gel column eluted with chloroform-methanol (9:1). Combination of the appropriate fractions gave E-5-(2-bromovinyl)-2'-deoxy-4'thio-uridine (90 mg, 75%) which was crystallised from methanol-water to give colourless crystals, m.p. 190°–191° C.

NMR SPECTRUM
($^1$H) δ (d$_6$DMSO): 11.63 (1H,s,NH), 8.20 (1H,s,H-6), 7.30 (1H,d,vinylic M,J=5 Hz), 6.97 (1H,d, vinylic H,J=5 Hz), 6.27-6.22 (1H,t,H-1'), 5.29-5.28 (1H,d,OH-3'), 5.24-5.20 (1H,t,OH-S') 4.40-4.32 (1H,m,H-3'), 3.69-3.16 (3H,m H-4', H-5'), 2.30-2.15 (2H,m,H-2')

UV SPECTRUM
max 249.7 nm (ε,16,000), 297.3 (ε,14,300)
min 271.2 nm (ε,7,700).

ELEMENTAL ANALYSIS
Found C,37.42: H, 3.72; N,7.76%. C$_{11}$H$_{13}$BrN$_2$O$_4$S requires
C,37.82: H, 3.72; N,8.02%.

MASS SPECTRUM
m/z 350 [M+H]$^+$, glycerol matrix

The α-anomer could be deblocked in an analogus manner to give E-5-(2-bromovinyl)-1-(2-deoxy-4'-thio-α-D-erythro-pentofuranosyl)uracil. This was crystallised from methanol;
m.p. 186°–187° C.

NMR SPECTRUM
($^1$H)δ(d$_6$DMSO): 11.56 (1H,s,NH), 8.44 (1H,s,H-6), 7.24 (1H,d,vinylic H, J=5 Hz), 6.86 (1H,d,vinylic H,J=5 Hz), 6.13-6.09 (1H,q,H-1'), 5.46-5.45 (1H,d,OH-3'), 5.06-5.02 (1H,t,OH-5'), 4.3-4.24 (1H,m, H-3'); 3.63-3.16 (3H,m, H-4'H-5'), 2.17- 2.09 (2H,m,M-2').

UV SPECTRUM
max 250.9 nm (ε,16,500), 296.2 nm (ε,14,300)
min 271.7 nm (ε,8,600).

MASS SPECTRUM
m/z 350 [M+H]$^+$, glycerol matrix.

EXAMPLE B

3',5'-Di-O-benzyl-2'-deoxy-5-iodo-β-4'-thiouridine

Mercuric bromide (370 mg; 1.03 mmol) and cadmium carbonate (480 mg; 2.8 mmol) were added to a stirred solution, protected from moisture, of benzyl 3,5-di-O-benzyl-2-deoxy-1,4-dithio-D-erythro-pentofuranoside (436 mg; 1.0 mmol) in dry MeCN (3 ml). A solution of 5-iodo-bis-O-trimethylsilyluracil (3 mmol) in MeCN (12 ml) was added via syringe. The progress of the reaction was monitored by analytical HPLC while the mixture was heated under reflux for 1 h. When cooled to ambient temperature, water (200 µl) was added and after stirring for 30 min. the suspension was filtered. The filtrate was evaporated and redissolved in dry MeCN, the precipitated 5-iodouracil was removed by filtration. The filtrate was purified by preparative HPLC on a 2.5 cm (1 in.) Zorbax C8 reverse phase column eluted at 20 ml min$^{-1}$ with a gradient [0–95% MeCN-water containing a constant 0.2% trifluoroacetic acid] over 20 min.; half-minute fractions were collected. Fractions containing pure product were pooled and evaporated to yield 330 mg of product as a gum. The anomer ratio was 2.8: 1,α:β as determined by 200 MHZ $^1$H-NMR. [CDCl$_3$ δ :8.72 (s, 0.26H, β-6-H); 8.55 (s, 0.74H, α-6-H); 6.35 (t, 0.26H, β-1'-H); 6.24 (dd , 0.74H, α-1'-H)]

EXAMPLE 2

2'-Deoxy-5-iodo-4'-thiouridine

The above product (240 mg; 0.44 mmol) dissolved in dry CH$_2$Cl$_2$ (10 ml+2 ml rinse) was added over 30 min to a stirred 1M solution of BCl$_3$ in CH$_2$Cl$_2$ (18 ml, 18 mmol) at −78° C. under N$_2$. The reaction was followed by analytical HPLC. After 6 h at −78° C., MeOH-CH$_2$Cl$_2$ (1:1, 18 ml) was added slowly and the mixture allowed to warm to ambient temperature then evaporated. The residue was re-evaporated from MeOH (3x) whereupon partial crystallisation occurred. The residue was taken up in MeO-CHCl$_3$ (1:1, 15 ml) and the solid collected by filtration, yield 7.7 mg of the desired β-anomer of the product. Mass spectrum m/z 370 (10%) for C$_9$H$_{11}$IN$_2$O$_4$S;200 MHz $^1$H-NMR δ : 11.2 (br s, 1H, NH); 8.48 (s, 1H, 6-H); 6.2 (t, 1H, 1'-H);5.23 (m,2H, 2xOH);4.35 (m, 1H 3'-H); 3.60 (t, 2H, 5'-H$_2$); 3.2 (4'-H, partly obscured by DOH); 2.20 (m, 2H, 2'-H $_2$). The filtrate yielded a further 40 mg of mixed α, β-anomers (ca. 1:1) from which pure β-anomer could be obtained by preparative HPLC.

EXAMPLE 3a

2'-Deoxy-5-ethyl-4'-thiouridine

Benzyl 3,5-di-O-benzyl-2-deoxy-1,4-dithio-D-erythro-pentofuranoside (5.6 mmol) was dissolved in CCl$_4$ (30 ml) and bromine (6.2 mmol) in CCl$_4$ (30 ml) was added. After stirring for 5 min. at ambient temperature the solvent was evaporated and the residue re-evaporated from CCl$_4$ (10 ml) to remove excess bromine. To a solution of this crude 1-bromothiosugar in CCl$_4$ (15 ml) was added bis-O-trimethylsilyl-5-ethyl uracil (16.6 mmol) [prepared by refluxing 5-ethyluracil (16.6 mmol) in a mixture of hexamethyldisilazane (50 ml) and chlorotrimethylsilane (5 ml) for 2 h., and evaporation of the solvents], HgBr$_2$ (1.99 g; 5.5 mmol) and CdCO$_3$ (2.36 g; 16.6 mmol). The solvent was evaporated and the residue heated at 100° C. for 1 h. The residue was worked up as for the thymidine analogue and the product purified by column chromatography. The benzyl ether protecting groups were removed by treatment with BCl$_3$ as described for the 5-iodo analogue.

EXAMPLE 3b

Separation of anomers of 2'-deoxy-5-ethyl-4'-thiouridine

The sample of the mixed α,β-anomers of the 5-ethyl compound were separated by preparative reverse phase HPLC on a 2.5 cm (lin.) Zorbax C8 column eluted with MeCN-H$_2$O (1:9, v/v); half-minute fractions were collected. The separate anomer pools were freeze dried.

β-Anomer: Yield 23 mg; retention time: 6.2 min.; mass spectrum m/z 272; talc. for C$_{11}$H$_{16}$N$_2$O$_4$S.0.3H$_2$O:C, 47.47; H,6.03; N; 10.06; found, C, 47.48; H, 5.71; N,9.96%; 200 MHz $^1$H-NMR, DMSO-d$_6$, δ : 11.28 (br s, 1H, NH); 7.8 (s, 1H, 6-H) 6.3 (t, 1H, 1'-H); 5.24 (d, 1H, 3'-OH); 5.16 (t, 1H, 5'OH); 4.37 (m, 1H, 3'-H); 3.62 (m, 2H, 5'-H$_2$); 3.3 (4'-H, partly obscured by DOH); 2.25-2.4 (q+m, 4H, CH$_2$CH$_3$+2'-H$_2$); 1.05 (t, 3H, CH$_2$CH$_3$).

α-Anomer: Yield 15.8 mg; retention time: 7.5 min.; mass spectrum m/z 272; calc. for C$_{11}$H$_{16}$N$_2$O$_4$S.H$_2$O:C, 45.51; H, 6.25; N. 9.65; found, C, 45.54; H, 5.75; N, 9.33%. 200 MHz $^1$H-NMR, DMSO-d$_6$,δ : 11.1 (br s, 1H, NH); 8.12 (s, 1H, 6-H); 6.2(q, 1H, 1'-H); 5.50 (d, 1H, 3'-OH); 5.00 (t, 1H, 5'-OH); 4.34 (m, 1H, 3'-H); 3.45-3.70 (m, 3H 4'-H+5'-H$_2$); 2.55 (m, 1H, 2'-H, partly obscured by solvent); 2.25 (q 2H, CH$_2$CH$_3$)2.05 (dt, 1H, 2'-H) 1.05 (t, 3H,CH$_2$CH$_3$).

EXAMPLE C

3'5'-Di-O-benzyl-5-bromo-2'deoxy'β-4'-thiouridine.

This compound was prepared by a method similar to the iodo compound above with the following modifications:

1. The total solvent (MeCN) volume for the reaction was 3 ml.
2. The CdCO$_3$ was omitted.
3. The excess of 5-bromo-bis-O-trimethylsilyuracil was reduced to 1.5 mole equivalents.

The yield of HPLC-purified compound was 193 mg; mass spectrum gave m/z 502 expected for C$_{23}$H$_{23}$BrN$_2$O$_4$S.

EXAMPLE 4

5-Bromo-2'-deoxy4'-thiouridine

The BCl$_3$ deprotection was conducted as for the iodocompound.

After HPLC purification a sample of the bromo-derivative (3.3 mg) of anomer ratio 3.6β:1α was obtained. Mass spectrum showed the expected molecular ions at 322(1%) and 324(0.8%); the 200 MHz $^1$H-NMR spectrum was consistent with the structure (DMSO-d6, 8.72(0.22H, s, α-H$_6$);8.48(0.78H,s, β-H$_6$).

EXAMPLE D

1-Acetoxy-3,5-di-p-toluoyl-2-deoxy-4-thio-D-erythro-pentofuranoside

A solution of benzyl 3,5-di-O-benzyl-2-deoxy-1-4-dithio-D-erythro-pentofuranoside (3.68 g; 8.76 mmol) in dry CH$_2$CH$_2$ (20 ml) was added dropwise to a stirred 1M solution of BCl$_3$ in CH$_2$Cl$_2$ (125 ml; 0.125 ml; 0.125 mol) at 78° C. under N$_2$. The mixture was stirred at −78° C. for 4.5 h, then a mixture of MeOH-CH$_2$Cl$_2$(1:1,v/v) was added slowly. After warming to room temperature the solvents were evaporated to give the crude O-debenzylated thiosugar. The gum was dissolved in dry pyridine at 0° C. under N$_2$ and a solution of p-toluoyl chloride (3.47 ml; 26.3 mmol) was added slowly. The mixture was stirred at 0° C. for 3 hours then the solvents were evaporated. The residue was dissolved in CH$_2$Cl$_2$, washed with 2M HCl, 1M Na$_2$CO$_3$ and water, dried over MgSO$_4$ and evaporated. The residue was purified by flash chromatography on SiO$_2$ eluted with EtOAc-hexane (1:9, v/v) to give the bis-toluoylthiosugar derivative (2.18 g;ca.50%): mass spectrum m/z 492. This product was dissolved in acetic anhydride (16 ml) and stirred at 0° C. Conc. H$_2$SO$_4$ (8 µl) was added followed after 10 min. by a second aliquot (8 µl); the reaction was monitored by TLC. After a further 55 min. stirring NaHCO$_3$ (100 mg.) was added and after 20 min. the mixture was cautiously poured into ice-water containing NaHCO$_3$. The product was extracted into CH$_2$Cl$_2$, dried and evaporated. The residue was purified by flash chromatography on SiO$_2$ eluted with 20–25% EtOAc-hexane. Yield 0.97g:- 200 MHz $^1$H-NMR DMSO-d6, δ:7.7–8.1 (m,4H,ArH); 7.1–7.4(m, 4H+solvent, ArH); 6.35 (dd,0.55H, 1-H);6.27(q,0.45H, 1-H);5.7–5.9 (m, 1H, 3-H); 3.7–4.7(m,3H,5-H$_2$+4-H); 2.2–2.7(m+2.2–2.7(m+2xs, 8H, 2×ArCH$_3$+2-H$_2$); 2.0–2.1 (2xs, 3H, CH$_3$CO-α & β). The anomer ratio was approximately 1.1/1; the material was sufficiently pure for use.

EXAMPLE 5

2'-Deoxy-5-propynyl-4'-thiouridine

5-Propynyluracil(0.112 g; 0.75 mmol) was heated in hexamethyldisilazane (3 ml) containing trimethylsilyl chloride (1 ml) until the solid dissolved (4 h). The solvents were evaporated and the residue dissolved in dry MeCN (6 ml). The solution was added, under N$_2$, to a stirred solution of the above thiosugar ester (0.2 g; 0.5 mmol) in MeCN (10 ml) at 0° C. Trimethylsilyl triflate (0.096 ml; 0.5 mmol) was added and the mixture stirred for 15 min. The mixture was diluted with CH$_2$Cl$_2$ (20 ml), poured into saturated aqueous NaHCO$_3$ and the organic layer separated. The aqueous layer was further extracted with CH$_2$Cl$_2$ and the combined organics dried and evaporated. Flash chromatography on SiO$_2$ eluted with EtOAc-hexane (3.2, v/v) gave the protected thionucleoside as a mixture of anomers (1.47/1 α/β) contaminated with a little propynyluracil. Yield 0.21 g. This material (0.206 g; 0.397 mmol) was dissolved in MeOH (15 ml) containing NaOMe (0.021 g; 0.397 mmol) and the mixture kept at ambient temperature overnight. The solution was neutralised with Dowex 50(H$^+$)ion-exchange resin, filtered and the filtrate evaporated to dryness. The solid was washed with ether (3×4 ml) and digested with hot acetone to give the required product as a white solid. Yield 100 mg. Methanol was added to the mixture and the solid was filtered off to give the pure β-anomer, 30 mg. The filtrate was processed by HPLC as described above to give a further 6 mg. of the β-anomer and a quantity of the α-anomer.

β-Anomer: mass spectrum m/z 282;200 MHz $^1$H-NMR, DMSO-d$_6$, δ: 11.55 (br s, 1H, NH); 8.7 (s, 1H, 6-H); 6.25 (t, 1H, 1'-H); 5.2(m, 2H, 2×OH); 4.3 (m, 1H, 3'-H); 3.6(m, 2H, 5'-H); 3.3 (4'-H, partially obscured by DOH); 2.15, (m, 2H, 2'-H); 2.0(s, 3H, C≡CCH$_3$).

5-Propynyluracil may be obtained from 5-iodouracil using the methodology analogous to that described by M. J. Robins et al (ibid).

EXAMPLE 6

2'-Deoxy-5-chloro-4'-thiouridine:

Starting with 5-chlorouracil, this compound was prepared in a similar manner to that described in Example 5. 5-chlorouracil is commercially available.

The compound was purified by HPLC as described above and obtained as mixture of anomers β/a ca. 3:1 $^1$H-200 MHz NMR DMSO-d$_6$, δ:11.8 (br s, 1H, NH); 8.65 (s, 0.25H, α-6-H); 8.4 (s, 0.75H, β-6-H); 6.1–6.3 (t+m, 1H, 1'-H); 5.55(d,0.25H, α-3'-OH) ;5.2–5.3(m, 1.5H,β-3'-OH+β-5'-OH); 5.05 (t,0.25H, α-5'-OH); 4.3–4.45 (m, 1H, 3'-H); 3.6–3.7 (m, 2H, 5' -H$_2$);2.1–2.4(m, 2H, 2'-H$_2$); 4'-H obscured by solvent.

Mass spectrum: observed m/z 278 and 280 for C$_9$H$_{11}$ClN$_2$O$_4$S.

EXAMPLE 7

2'-Deoxy-5-trifluoromethyl-4'-thiouridine:

Starting with 5-trifluoromethyluracil, this compound was prepared in a similar manner to that described in Example 5. 5-trifluoromethyluracil is commercially available. A sample of this compound of anomer ratio β/α ca. 8:1 was obtained by trituration of the crude deprotected nucleoside mixture with acetone, filtration and evaporation. $^1$H-200 MHz NMR DMSO-d$_6$, δ:11.8 (br s, 1H, NH); 8.83 (s, 1H, β-6-H); 6.2 (t, 1H, β-1'-H); 5.2–5.4 (m, 2H, β-3'+5'-OH); 4.25–4.4 (m, 1H, β-3'-H); 3.5–3.8 (m, 2H, β5'H); 3.0–3.5 (m, 4'H obscured by solvent); 2.2–2.4 (m, 2H, β-5'-H$_2$); small signals indicative of the α-anomer content were also observed.

Mass spectrum: observed m/z 312 for C$_{10}$H$_{11}$F$_3$N$_2$O$_4$S.

EXAMPLE 8

2'-Deoxy-5-ethynyl-4'-thiouridine:

Starting with 5-ethynyluracil, this compound was prepared in a similar manner to that described in Example 5. 5-ethynyluracil may be prepared from 5-ioduracil using the methodology analogous to that described by M. J. Robins et al (ibid).

A sample of the pure β-anomer of this compound was obtained by boiling the crude anomer mixture with MeOH and filtering off the product.

$^1$H-200 MHz NMR DMSO-d$_6$ δ: 11.6 (br s, 1H, NH); 8.42 (s, 1H, β-6-H); 6.23(t, 1H, β-1'-H); 5.1–5.35 (m, 2H, β-3'+ 5'-OH); 4.25–4.45 (m, 1H, β-3'-H); 4.15 (s, 1H≡CH); 3.55–3.75 (m,2H, β-5'-H); 3.1–3.5 (β-4'H, obscured by DOH); 2.1–2.4 (m,2H, β- 5'-H$_2$).

Mass spectrum: observed m/z 268 for C$_{11}$H$_{11}$N$_2$O$_4$S.

EXAMPLE 9

2'-Deoxy-5-E-(2-bromovinyl)-4'-thiocytidine.

To a solution of benzyl 3,5-di-O-benzyl-2-deoxy-1,4-dithio-D-erythro-pentofuranose (4 g; 9.5 mmol) in acetic acid (50 ml) and acetic anhydride (50 ml) was added conc. sulphuric acid (50 μl) and the mixture stirred at ambient temperature for 30 min. when TLC (EtOAc-hexane, 1:4, v/v) showed complete conversion to a more polar sugar. The mixture was poured into excess sodium bicarbonate Na$_2$HCO$_3$, extracted with CHCl$_3$, the extracts dried over MgSO$_4$ and evaporated. The residue was purified by column chromatography on SiO$_2$ in the TLC solvent to give the 1'-acetoxy-di-O-benzylthiosugar derivative (1.84 g; 54%) which was used directly below. To the above derivative (0.33 g; 0.89 mmol) in dry CH$_2$Cl$_2$ (3 ml) at 0° C. was added SnCl$_4$ (0.33 g; 0.89 mmol) in dry CH$_2$Cl$_2$ (3 ml) and E-5-(2-bromovinyl)-2,4-dimethoxypyrimidine (0.218 g; 0.89 mmol) in dry CH$_2$Cl$_2$ (3 ml). The stirred mixture was allowed to warm to ambient temperature and stirred for a further 4 h. The mixture was poured onto water, washed with saturated NaHCO$_3$ and dried over MgSO$_4$. After evaporation, the residue was chromatographed on SiO$_2$ in toluene-acetone (9:1, v/v) to give the pure β-anomer of the protected thionucleoside, which was crystallised from MeOH (ca 40 mg). NMR, DMSO-d$_6$, δ:8.31 (s, 1H, H-6); 7.39-7.28 (s, 10H, 2Ph); 7.0 (d, 1H, vinyl H, J=14 Hz); 6.85 (d, 1H, vinyl H,J=14 Hz); 6.27 (t, 1H, 1'-H); 4.56 (s, 4H, 2PhCH$_2$); 4.33 (m, 1H, 3'-H); 3.90 (s, 3H, OCH$_3$); 3.77 (m, 2H, 5'-H$_2$); 3.63 (m, 1H, 4'-H), 2.50 (m, 2H, 2'-H$_2$).

The above methoxy derivative of the protected thionucleoside was converted to the cytidine analogue by dissolution in NH$_3$/MeOH at ambient temperature for 2d. The product was isolated by column chromatography on SiO$_2$ eluted with CHCl$_3$-MeOH (9:1, v/v), then deprotected directly with BCl$_3$ as described above. The product was essentially pure and consisted of the HCl salt of the mixture of anomers in the approximate ratio 95:5, β:α by HPLC on Zorbax C8 eluted with a 0–95% gradient of MeCN in water over 15 min. followed by 95% MeCN: retention times β 16.3 min.; α 18.11 min. 200 MHz $^1$H-NMR, DMSO-d6, δ: 8.55 (s, 1H, 6-H); 7.25 (d, 1H, J$_{trans}$ 13.8 Hz, vinyl H); 6.95 (d, 1H, J$_{trans}$ 13.8 Hz, vinyl H); 6.18 (t, 1H, 1'-Hβ). Mass spectrum (EI): no molecular ion was observed but characteristic ions for the base [215,217 for C$_6$H$_6$BrN$_3$O; 136 for C$_6$H$_6$N$_3$O] and the thiosugar [85,C$_5$H$_3$S] were seen.

A pure sample of the free base of the β-anomer was obtained by preparative HPLC as described above.

200 MHz $^1$H-NMR, DMSO-d6, δ: 8.18 (s, 1H, 6-H); 7.1–7.4 (br s, 2H, NH$_2$); 7.05 (d, 1H, J$_{trans}$ 14.5 Hz, vinyl H); 6.85 (d, 1H, J$_{trans}$ 14.5 Hz, vinyl H); 6.30 (t, 1H, 1'-H); 5.1–5.25 (m, 2H, 2×OH); 4.3–4.45 (m, 1H, 3'-H); 3.55–3.7 (m,2H, 5'-H$_2$); 3.0–3.4 (4'-H obscured by DOH); 2.1–2.35 (m,2H, 2'-H$_2$).

EXAMPLE 10

2'-Deoxy-5-propyl-4'-thiouridine:

2'-Deoxy-5-propynyl-4'thiouridine, β-anomer, (26 mg) and 5% Pd/C (40 mg) in MeOH (80 ml) was stirred in an atmosphere of hydrogen for 45 min. HPLC analysis showed complete conversion to a more lipophilic compound. The mixture was filtered and evaporated to give a gum, yield 25 mg. Trituration with ether-hexane gave the product as a white solid. 200 MHz $^1$H-NMR, DMSO-d6, δ:11.25 (br s, 1H, NH); 7.80 (s, 1H, β-6-H); 6.27 (t, 1H, β-1'H); 5.22 (d, 1H, β-3'-OH); 5.14 (m, 1H, β-5'-OH); 4.3–4.45 (m, 1H, β-3'-H); 3.55– 3.75 (m, 2H, β-5'-H); 3.2–3.4 (β-4'H, obscured by DOH); 2.1– 2.35 (m, 4H, β-5'-H$_2$+ CH$_2$CH$_2$Me); 1.45 (m, 2H, CH$_2$CH$_2$Me); 0.88 (t, 3H, CH$_3$).

Mass spectrum: m/z 286 (M$^+$) for C$_{12}$H$_{18}$N$_2$O$_4$S

EXAMPLE 11

E-2'-Deoxy-5-(propen-1-yl)-4'-thiouridine (a) 5-Allyluracil.

Uracil (1 g; 9 mmol) was dissolved in water (200 ml) at 70° C. and Hg(OAc)$_2$ (2.9 g; 9.1 mmol) was added. The mixture was stirred at 70° C. for 1 week. After cooling to ambient temperature NaCl (1.5 g) was added and the mixture stirred for 4 h. The resulting thick suspension of 5-chloromercuryuracil was filtered, the solid washed with 0.1M NaCl solution and dried in vacuo at 85° C. for 2 days (2.27 g). To the crude solid (1 g; 2.9 mmol) in MeCN (25 ml) was added Li$_2$PdCl$_4$ (0.76 g) and allyl chloride (2.9 ml) and the mixture stirred at ambient temperature for 1 week. The suspension was filtered and the filtrate evaporated to dryness. The residue was dissolved in MeOH (75 ml) and treated with H$_2$S gas; the black precipitate of HgS was removed by filtration and the filtrate was evaporated to leave a white solid. The desired product was isolated by flash chromatography on SiO$_2$ eluted with 8% MeOH-CH$_2$Cl$_2$ (v/v). Yield (85 mg, 20%): Mass spectrum gave m/z 152 for C$_7$H$_8$N$_2$O$_2$ (M$^+$); 200 MHz 1H-NMR DMSO-d$_6$, δ: 10.9 (br s, 1H, NH); 7.16 (s, 1H, 6-H); 5.7–6.0 (m, 1H, —CH=); 4.95–5.15 (m, 2H=CH$_2$); 4.33 (br s, 1H, NH); 2.92 (d, 2H, CH$_2$).

(b) 5-[E-propen-1-yl] uracil

To a solution of 5-allyluracil (80 mg; 0.5 mmol) in 95% aq. EtOH (50 ml) was added (Ph$_3$P)$_3$RhCl (90 mg; 0.1 mmol) and the mixture heated under reflux for 3 days. The solvent was evaporated and the product isolated by flash chromatography on SiO$_2$ eluted with 5% MeOH-CH$_2$Cl$_2$. Yield 56 mg 70%; 200 MHz 1H-NMR DMSO-d$_6$, δ: 11.0 (br s, 1H, NH); 7.42 (s, 1H, 6-H); 6.35–6.55 (qq, 1H =CH-Me); 5.95–6.1 (dd, 1H, —CH=); 1.74 (dd, 3H, CH$_3$).

(c) E-2'-Deoxy-5-(propen-1-yl)-4'-thiouridine 5-(E-propen-1-yl)uracil (110 mg; 0.78 mmol) was converted to the bis-TMS-ether, coupled with the protected thiosugar and deprotected with methoxide as described for the 5-propynyl analogue. The crude product was purified by chromatography on SiO$_2$ eluted with 5% MeOH-CH$_2$Cl$_2$. Yield 11.8 mg of mixed anomers in the ratio 1.2:1 α:β. 200 MHz 1H-NMR DMSO-d$_6$, δ: 11.35 (br s, 1H, NH); 8.35 (s, 0.55H, α-6-H); 8.05 (s, 0.45H, β-6-H); 6.0–6.6 (m, 3H, 1'-H+—CH=CH—); 5.5 (d, 0.55H, α-3'-OH); 5.1–5.3 (d+t, 0.9H, β-5'-OH+β-3'-OH); 5.0 (t, 0.55H, α-5'-OH); 4.38 (m, 1H, 3'-H); 3.1–3.7 (m, 5'-H$_2$+4'-H, partially obscured by DOH); 2.0–2.6 (m, 2'-H$_2$, partially obscured by solvent); 1.75 (d, 3H, CH$_3$).

Mass spectrum: m/z 284 (M$^+$) for C$_{12}$H$_{16}$N$_2$O$_4$S

EXAMPLE E

Preparation of
E-5-(2-bromovinyl)-Uracil-5-Bromo-2,4-dimethoxypyrimidine

A solution of 5-bromo-2,4-dichloropyrimidine (16 g: 70.2 mmol) [D. M. Mulvey et al. J. Het. Chem., 1973,p79] in dry MeOH (55 ml) was added slowly to a stirred solution of sodium (3.23 g: 140.4 mmol) in MeOH (55 ml) at 0° C. over 30 min. The ice-bath was removed and the reaction mixture stirred at ambient temperature for 18 h. The precipitated salt was removed by filtration and the filtrate evaporated to give an oil. To this was added an aqueous solution of NaOH (30 ml; 30% w/v); the product separated as an upper layer and was extracted into Et20. The organic extracts were dried over MgSO$_4$ and evaporated. The residue was crystallised from thanol to give the product as colourless plates, yield 14.3 g, 93%, mp 62°–63° C. Mass spectrum, elm/z 219 (M$^+$, 11%). Analysis, found: C,33.20, H,3.26, Br 36.90, N, 12.7%; C$_6$H$_7$BrN$_2$O$_2$ requires: C,32.90, H,3.33, Br 36.50, N, 12.80%.

5-Formyl-2,4-dimethoxypryrimidine

A solution of 1.6M n-BuLi in hexane (48 ml, 73.6 mmol) was added over 5 min. to a stirred suspension of 5-bromo-2,4-dimethoxypyrimidine (16 g; 72.9 mmol) in dry Et$_2$O (240 ml) at −70° C. under an atmosphere of dry N$_2$. Dry ethyl formate (28 g: 377 mmol) was added and the orange solution stirred at −70° C. for 1 h then allowed to warm slowly to ambient temperature. Water (400 ml) was added and the aqueous layer separated and extracted with Et$_2$O (3×200 ml). The ether layer was combined with the extracts and dried over MgSO$_4$, filtered and evaporated. The residue was purified by column chromatography by preloading in SiO$_2$ and eluting with EtOAc-hexane (3:7, v/v). Product fractions were combined and evaporated to give fine white needles, yield 6.89 g, (56%). Mass spectrum m/z 169 (M+H)$^+$ Analysis, found: C, 50:1;H,4.5;N, 16.9%;C$_7$H$_8$N$_2$O$_3$ requires C,50.00; H,4.79; N, 16.66%

E-5-(2-carboxyvinyl)-2,4-dimethoxypyrimidine

Malonic acid (13.03 g; 126.2 mmol) and redistilled piperidine (2 ml) were added to a solution of 5-formyl-2,4-dimethoxypyrimidine (10.52 g; 6.2.6 mmol) in dry pyridine (60 ml). The mixture was heated on a steam bath for 10 h then the solvent was removed by distillation under reduced pressure. The residual oil was re-evaporated from water (3×25 ml) and the solid thus obtained recrystallised firstly from water and then from dry methanol to give the product as white needles, yield 6.45 g; a second crop was obtained from the filtrate (1.08 g). Total yield 7.53g (57%). Mass spectrum: (El) m/z 210 (M$^+$). Analysis, found: C,52.1;H, 4.8;N, 13.1%: C$_9$H$_{10}$N$_2$O$_4$ requires: C, 52.43; H, 4.79; N, 13.33%.

E-5-(2-Bromovinyl)-2,4-dimethoxypyrimidine

To a solution of E-5-(2-carboxyvinyl)-2,4-dimethoxypyrimidine (0.300 g; 1.43 retool) in dry DMF (5 ml) was added K$_2$CO$_3$ (0.45 g: 5.25 mmol). After stirring at ambient temperature for 15 min. a solution of N-bromosuccinimide (0.258 g; 1.45 mmol) in dry DMF (4 ml) was added dropwise over 10 min. The suspension was immediately filtered, the solid washed with DMF and the filtrate evaporated in high vacuum. The solid residue was purified by column chromatography by preloading on SiO$_2$ and eluting with EtOAc-hexane (7:3, v/v). Product fractions were pooled and evaporated to give fine white crystals, yield 0.561 g (45%). FAB mass spectrum: m/z245 and 247 (M+H)$^+$. Analysis, found: C,39.9; H, 3.6; N, 11.5% C$_8$H$_9$BrN$_2$O$_2$ requires C, 40.20; H, 3.70; N. 11.43%.

E-5-(2-Bromovinyl)uracil

To a solution of E-5-(2-bromovinyl)-2,4-dimethoxypyrimidine (2.45 g; 10 mmol) in AcOH (10 ml) was added NaI (3.3 g; 2.2 eq.; 22 mmol) and the solution heated under reflux for 3 h. The hot mixture was filtered and diluted with water (15 ml). After cooling, the precipitated product was filtered off, washed with acetone (50 ml) and ether (20 ml) and dried to give a pale yellow powder (1.40 g, 65%). Mp>320° C.; 60 MHz $^1$H-NMR, DMSO-6d, δ: 7.60 (s, 1H, H-6); 7.30 (d, 1H, J=13 Hz, vinyl H); 6.80 (d, 1H, J=13 Hz, vinyl H).

BIOLOGICAL DATA a) Anti-HSV Activity

Herpes Simplex Virus types 1 (HSV 1) and 2 (HSV2) were assayed in monolayers of Veto cells in multiwell trays. The virus strains used were SC16 and 186 for HSV-1 and HSV-2 respectively. Activity of compounds was determined in the plaque reduction assay, in which a cell monolayer was infected with a suspension of the appropirate HSV, and then overlaid with nutrient agarose in the form of a gel to ensure that there was no spread of virus throughout the culture. A range of concentrations of compound of known molarity was incorporated in the nutrient agarose overlay. Plaque numbers at each concentration were expressed as percentages of the control and a dose-response curve was drawn. From this curve the 50% inhibitory concentration ($IC_{50}$) was estimated to be 0.66 μm for the compound of formula (I) in which X represents a 2-bromovinyl group.

b) Anti-CMV Activity

Human cytomogalovirus (HCMV) was assayed in monolayers of either MRC5 cells (human embryonic lung) in multiwell trays. The standard CMV strain AD 169 was used. Activity of compounds is determined in the plaque reduction assay, in which a cell monolayer is infected with a suspension of HCMV, and then overlaid with nutrient agarose in the form of a gel to ensure that there is no spread of virus throughout the culture. A range of concentrations of compound of known molarity was incorporated in the nutrient agarose overlay. Plaque numbers at each concentration of drug are expressed as percentage of the control and a dose-response curve is drawn.

c) Anti-VZV Activity

Clinical isolates of varicella zoster virus (VZV) were assayed in monolayers of MRC-5 cells. MRC-5 cells are derived from human embyonic lung tissue. A plaque reduction assay was used in which a suspension of the virus stock was used to infect monolayers of the cells in multiwell trays. a range of concentrations of the compound under test of known molarity was added to the wells. Plaque numbers at each concnetration were expressed as percentages of the control and a dose response curve was constructed. From these curves the 50% inhibitory concentration of each drug was determined.

Table 1 shows the activity of compounds of the invention.

TABLE 1

Activity of compounds of the invention against HSv1, HSV2 and VSV. Data relates to the β-anomers.

| COMPOUND | | HSV1 | HSV2 | VZV | CCID50 |
|---|---|---|---|---|---|
| X | Y | | IC50 (μM) | | μM |
| CH=CHBr | OH | 0.6 | >10, <100 | 0.1, 0.08, 0.18 | >500 |
| $CH_2CH_3$ | OH | 0.17, 0.25, 0.52 | 5, 2.3 | 0.79, 0.99 | >100, 253 |
| CH=CHBr | $NH_2$ | −2.3 | >10 | | |

EXAMPLES

The following examples illustrate pharmaceutical formulations according to the invention in which the active ingredient is a compound of formula (I).

| Formulation Example A Tablet | |
|---|---|
| Active ingredient | 100 mg |
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

| Formulation Example B Opthalmic Solution | |
|---|---|
| Active ingredient | 0.5 g |
| Sodium chloride, analytical grade | 0.9 g |
| Thiomersal | 0.001 g |
| Purified water to | 100 ml |
| pH adjusted to | 7.5 |

Formulation Example C: Tablet Formulations

The following formulations a and b are prepared by wet granulation of the ingredients with a solution of povidone, followed by addition of magnesium stearate and compression.

| | mg/tablet | mg/tablet |
|---|---|---|
| Tablet Formulation a | | |
| (a) Active ingredient | 250 | 250 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 500 | 300 |
| Tablet Formulation b | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Tablet Formulation c | | |
| Active ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients. The lactose used in formulation E is of the direct compression type.

| | mg/capsule |
|---|---|
| Tablet Formulation d | |
| Active Ingredient | 250 |
| Pregelatinised Starch NF15 | 150 |
| | 400 |
| Tablet Formulation e | |
| Active Ingredient | 250 |
| Lactose | 150 |
| Avicel | 100 |

-continued

| | mg/capsule |
|---|---|
| | 500 |

Tablet Formulation f (Controlled Release Formulation)

The formulation is prepared by wet granulation of the ingredients (below) with a solution of povidone followed by the addition of magnesium stearate and compression.

| | | mg/tablet |
|---|---|---|
| (a) | Active Ingredient | 500 |
| (b) | Hydroxpropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

Drug release takes place over a period of about 6–8 hours and was complete after 12 hours.

Formulation Example D: Capsule Formulations

Capsule Formulation a

A capsule formulation is prepared by admixing the ingredients of Formulation D in Example C above and filling into a two-part hard gelatin capsule. Formulation B (infra) is prepared in a similar manner.

| | mg/capsule |
|---|---|
| Capsule Formulation b | |
| (a) Active ingredient | 250 |
| (b) Lactose B.P. | 143 |
| (c) Sodium Starch Glycollate | 25 |
| (d) Magnesium Stearate | 2 |
| | 420 |
| Capsule Formulation c | |
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into a two-part hard gelatin capsule.

| Capsule Formulation d | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Capsule Formulation e (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

Formulation Example E; Injectable Formulation

| | |
|---|---|
| Active ingredient | 0.200 g |
| Sterile, pyrogen free phosphate buffer (pH 7.0) to | 10 ml |

The active ingredient is dissolved in most of the phosphate buffer (35°–40° C.), then made up to volume and filtered through a sterile micropore filter into a sterile 10 ml amber glass vial (type 1) and sealed with sterile closures and overseals.

| Formulation Example F: Intramuscular injection | |
|---|---|
| Active Ingredient | 0.20 g |
| Benzyl Alcohol | 0.10 g |
| Glucofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

| Formulation Example G: | Syrup Suspension |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

| Formulation Example H: Suppository | mg/suppository |
|---|---|
| Active Ingredient (63 μm)* | 250 |
| Hard Fat, BP (Witepsol H15 - Dynamit NoBel) | 1770 |
| | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

| Formulation Example I: Pessaries | mg/pessary |
|---|---|
| Active ingredient 63 μm | 250 |
| Anydrate Dextrose | 380 |
| Potato Starch | 363 |
| Magnesium Stearate | 7 |
| | 1000 |

The above ingredients are mixed directly and pessaries prepared by direct compression of the resulting mixture.

We claim:

1. 2'-Deoxy-5-ethyl-4'-thio-β-uridine of the formula (I):

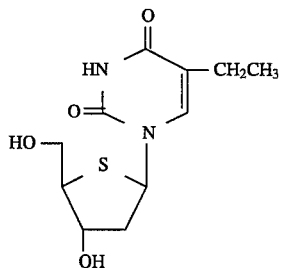

and physiologically functional salt and ester derivatives.

2. A pharmaceutical composition comprising a compound of claim 1 in association with a pharmaceutically acceptable carrier or diluent.

3. The composition of claim 2 in unit dosage form.

4. The unit dosage form of claim 3 in the form of a tablet or capsule.

5. A method of treating a herpes virus infection of the human or animal body which comprises administering to a human or animal in need of such treatment a therapeutically effective amount of 2'-deoxy-5-ethyl-4'-thio-β-uridine.

6. A method of treating shingles or chicken pox which comprises administering to a human with shingles or chicken pox a therapeutically effective amount of 2'-deoxy-5-ethyl-4'-thio-β-uridine.

7. The method of claim 5 wherein the herpes virus is selected from HSV-1, HSV-2, HHV-6, VZV, CMV and EBV.

8. The method of claim 5 wherein the herpes virus is HSV-1 or HSV-2.

9. The method of claim 5 wherein the effective amount administered is from 1 to 100 mg per kg body weight per day.

10. The method of claim 9 wherein the effective amount administered is from 5 to 30 mg per kg body weight per day.

11. A physiologically functional derivative of 2'-deoxy-5-ethyl-4'-thio-β-uridine in the form of a salt or ester.

12. The physiologically functional derivative of claim 11 which is selected from the group consisting of alkali metal, alkaline earth metal, ammonium, tetra($C_{1-4}$ alkyl)ammonium, hydrochloride and acetate salts and mono- and di-carboxylic acid esters.

13. A pharmaceutical composition comprising a compound of claim 11 with a pharmaceutically acceptable carrier or diluent.

14. The composition of claim 13 in unit dosage form.

15. The unit dosage form of claim 14 in the form of a tablet or capsule.

16. A method of treating a herpes virus infection of the human or animal body which comprises administering to a human or animal in need of such treatment a therapeutically effective amount of a compound of claim 11.

17. A method of treating shingles or chicken pox which comprises administering to a human with shingles or chicken pox a therapeutically effective amount of a compound of claim 12.

18. The method of claim 16 wherein the herpes virus is selected from HSV-1, HSV-2, HHV-6, VZV, CMV and EBV.

19. The method of claim 16 wherein the herpes virus is HSV-1 or HSV-2.

20. The method of claim 16 wherein the effective amount administered is from 1 to 100 mg per kg body weight per day.

21. The method of claim 20 wherein the effective amount administered is from 5 to 30 mg per kg body weight per day.

* * * * *